(12) United States Patent
Tsilibary et al.

(10) Patent No.: US 6,780,603 B1
(45) Date of Patent: Aug. 24, 2004

(54) ANALYSIS OF ALPHA INTEGRINS FOR THE DIAGNOSIS OF DIABETIC NEPHROPATHY

(75) Inventors: Photini-Effie Tsilibary, Minneapolis, MN (US); Aristidis S. Charonis, Minneapolis, MN (US); Suman Setty, Minneapolis, MN (US); Michael Mauer, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/000,004
(22) PCT Filed: Jul. 19, 1996
(86) PCT No.: PCT/US96/12067
 § 371 (c)(1),
 (2), (4) Date: May 2, 2001
(87) PCT Pub. No.: WO97/04133
 PCT Pub. Date: Feb. 6, 1997

Related U.S. Application Data
(60) Provisional application No. 60/016,700, filed on May 2, 1996, provisional application No. 60/001,861, filed on Aug. 3, 1995, and provisional application No. 60/001,387, filed on Jul. 21, 1995.

(51) Int. Cl.$^7$ .............................................. G01N 33/53
(52) U.S. Cl. ...................... 435/7.21; 435/7.24; 435/975
(58) Field of Search .............................. 435/7.21, 7.24, 435/975

(56) References Cited

U.S. PATENT DOCUMENTS 4,894,326 A * 1/1990 Matsuura et al. .............. 435/7

OTHER PUBLICATIONS

Sternberger, Immunocytochemistry, Prentice–Hall, Inc., 1974. pp. 45–54.*
Baraldi, et al. *Nephron* 1992; 6294):382–388, "Very late activation–3 integrin is the dominant .beta. 1–integrin on the glomerular capillary wall: an immunofluorescence study in nephrotic syndrome".
Briesewitz, et al. *Journal of Biological Chemistry* Feb. 1993; 268(4):2989–2996, "Expression of native and truncated forms of the human Integrin alpha–1 subunit".

Ignatius, et al. *J. Cell. Biol.* Aug. 1990; 111:709–720, "Molecular cloning of the rat integrin alpha 1 subunit".
Kyu Jin, et al. *J. Am. Soc. Nephrology* 1994: 5(3):966, "Skin fibroblast integrin expression in IDDM".
Mendrick, et al. *Laboratory Investigation* Mar. 1995; 72(3):367–375, "Glomerular epithelial and mesangial cells differentially modulate the binding specificities of VLA–1 and VLA–2".
Nuovo, G.J., et al. *PCR Methods and Applications* Nov. 1, 1992; 2(2):117–123, "In situ localization of PCR–amplified human and viral cDNAs".
Robbins, et al. *Investigative Ophtalmology and Visual Science* Aug. 1994; 35(9):3475–3485, "Immunolocalisation of integrins i proliferative retinal membranes".
Roth, et al.*Proceedings of the National Academy of Sciences of the United States of America* Oct. 15, 1993; 90(20):9640–9644, "Integrin overexpression induced by high glucose and by human diabetes: potential pathway to cell dysfunction in diabetic microangiopathy".
Rozzo, et al. *FEBS Letters* Oct. 1993; 332(3):263–267, Amsterdam NL, "Modulation of integrin heterodimers during human neuroblastoma cell differenciation".
Setty, et al. *Cell Adhesion and Communication* Aug., 1995; 3(3):187–200, "Glucose–induced alteration of integrin expression and function in cultured human mesangial cells".
Setty, et al. *Annual Meeting of the American Society of Mephrology, San Diego, California*, USA Nov. 5–8, 1995; *Journal of the American Society of Nephrology* 1995; 6(3):911, "Altered mesangial expression of integrin genes in response to elevated glucose and experimental diabeters".
Shikata, et al., *American Jouranl of Kidney Diseases* May 1995; 25(5):680–688, "Distribution of extracellular matrix receptors in various forms of glomerulonephritis".
Takada, et al. *J. Cell Biol.* Jul. 1989; 109:397–407, "The primary structure of the VLA–2/collagen receptor alpha 2 subunit".

* cited by examiner

*Primary Examiner*—David Saunders
(74) *Attorney, Agent, or Firm*—Merchant & Gould P.C.

(57) ABSTRACT

Analysis of alterations in integrin subunit expression, particularly α1 and/or α2 integrin subunit expression from integrin producing cells as compared to normal controls as a diagnostic method to identify individuals who have or are predisposed to pathologies associated with altered matrix deposition, such as diabetic renal nephropathy.

8 Claims, 1 Drawing Sheet

SEQUENCE LISTING

```
<160> NUMBER OF SEQ ID NOS: 16

<210> SEQ ID NO 1
<211> LENGTH: 3989
<212> TYPE: DNA
<213> ORGANISM: Rattus
<220> FEATURE:
<221> NAME/KEY: CDS
<222> LOCATION: (420)..(3959)
<223> OTHER INFORMATION:

<400> SEQUENCE: 1
agtatggaga gaaggtcgtt taaaaaggca gatgtccctt taaggtttgc tttgctgctg      60
cccgtggact ttagcctaaa cagggtcccg cgaagttggc tttatttgtc catgtctcgg     120
acacagcctg ggtagctgcc agtgagattt cagggacgga gcgcgcaaag ggggggaaa     180 tgtggcaatc catctgggat gtgagacgcg tggagagggc ttagcagcat ttgaccaaaa     240
```

-continued

```
cacaggaaat cactcctcca cagctcctgg gcgcagcagc ggctgggggcc actgccggac      300 accctcggag accacacgag tgacccagag cgcaagtcgc cagcgtcccg gttctgcctg      360
ttcctgccag ctcctgccca cgaaccggca cgtagctggt tccagcagcc gctccagca       419 atg gtc ccc agg cgt cct gcc agc cta gag gtc act gta gcc tgc ata        467
Met Val Pro Arg Arg Pro Ala Ser Leu Glu Val Thr Val Ala Cys Ile
1               5                   10                  15 tgg ctt ctc acg gtc atc cta ggc ttc tgc gtc tcc ttc aat gtt gat        515
Trp Leu Leu Thr Val Ile Leu Gly Phe Cys Val Ser Phe Asn Val Asp
            20                  25                  30 gtg aaa aac tca atg agt ttc agt ggc cca gta gag gac atg ttt gga        563
Val Lys Asn Ser Met Ser Phe Ser Gly Pro Val Glu Asp Met Phe Gly
        35                  40                  45 tac act gtt caa caa tat gaa aac gaa gaa ggc aaa tgg gtt ctt att        611
Tyr Thr Val Gln Gln Tyr Glu Asn Glu Glu Gly Lys Trp Val Leu Ile
    50                  55                  60 ggt tct cct tta gtt ggc caa ccc aaa gca aga act gga gat gtc tat        659
Gly Ser Pro Leu Val Gly Gln Pro Lys Ala Arg Thr Gly Asp Val Tyr
65                  70                  75                  80 aag tgt ccg gtt ggg aga gag aga gca atg cct tgc gtg aag ttg gac        707
Lys Cys Pro Val Gly Arg Glu Arg Ala Met Pro Cys Val Lys Leu Asp
                85                  90                  95 ttg cca gtt aac aca tcg atc ccc aat gtc aca gaa ata aag gaa aac        755
Leu Pro Val Asn Thr Ser Ile Pro Asn Val Thr Glu Ile Lys Glu Asn
            100                 105                 110 atg aca ttt gga tca act tta gtc acc aac ccg aat gga gga ttt ctg        803
Met Thr Phe Gly Ser Thr Leu Val Thr Asn Pro Asn Gly Gly Phe Leu
        115                 120                 125 gca tgt ggg ccc ttg tat gcc tat aga tgt gga cat ttg cat tat aca        851
Ala Cys Gly Pro Leu Tyr Ala Tyr Arg Cys Gly His Leu His Tyr Thr
    130                 135                 140 act gga ata tgt tct gat gtc agt cct aca ttt caa gtt gtg aac tcc        899
Thr Gly Ile Cys Ser Asp Val Ser Pro Thr Phe Gln Val Val Asn Ser
145                 150                 155                 160 ttt gcc cct gta caa gaa tgc agc acc cag ctg gac ata gtc atc gtc        947
Phe Ala Pro Val Gln Glu Cys Ser Thr Gln Leu Asp Ile Val Ile Val
                165                 170                 175 ctg gat ggc tcc aac agc atc tac ccc tgg gaa agt gtc atc gcc ttt        995
Leu Asp Gly Ser Asn Ser Ile Tyr Pro Trp Glu Ser Val Ile Ala Phe
            180                 185                 190 tta aac gac ctt ctt aag agg atg gat att ggc cct aag cag aca cag       1043
Leu Asn Asp Leu Leu Lys Arg Met Asp Ile Gly Pro Lys Gln Thr Gln
        195                 200                 205 gtc ggg att gta cag tat gga gag aat gta acc cat gag ttc aac ctc       1091
Val Gly Ile Val Gln Tyr Gly Glu Asn Val Thr His Glu Phe Asn Leu
    210                 215                 220 aat aag tat tca tcc aca gaa gag gtc ctt gtc gca gca aac aaa ata       1139
Asn Lys Tyr Ser Ser Thr Glu Glu Val Leu Val Ala Ala Asn Lys Ile
225                 230                 235                 240 ggc cga cag gga ggc ctc caa acg atg aca gcc ctt gga ata gac aca       1187
Gly Arg Gln Gly Gly Leu Gln Thr Met Thr Ala Leu Gly Ile Asp Thr
                245                 250                 255 gcc agg aaa gag gca ttc act gaa gct cgg ggt gcc agg agg gga gtt       1235
Ala Arg Lys Glu Ala Phe Thr Glu Ala Arg Gly Ala Arg Arg Gly Val
            260                 265                 270 aaa aaa gtc atg gtt att gtg acc gac gga gaa tcg cat gac aac tat       1283
Lys Lys Val Met Val Ile Val Thr Asp Gly Glu Ser His Asp Asn Tyr
        275                 280                 285 cgc ctg aaa cag gtc atc caa gac tgc gag gac gaa aac att cag cga       1331
```

```
Arg Leu Lys Gln Val Ile Gln Asp Cys Glu Asp Glu Asn Ile Gln Arg
    290                 295                 300 ttt tcc ata gct atc ctt ggc cac tat aac agg ggg aac tta agc act      1379
Phe Ser Ile Ala Ile Leu Gly His Tyr Asn Arg Gly Asn Leu Ser Thr
305                 310                 315                 320 gaa aaa ttt gtg gag gaa ata aaa tcg atc gca agc gag ccc acg gaa      1427
Glu Lys Phe Val Glu Glu Ile Lys Ser Ile Ala Ser Glu Pro Thr Glu
                325                 330                 335 aag cac ttc ttc aat gtc tcg gat gag ttg gcc ctg gtc act att gtt      1475
Lys His Phe Phe Asn Val Ser Asp Glu Leu Ala Leu Val Thr Ile Val
            340                 345                 350 aaa gct ctg gga gaa agg ata ttc gct ttg gaa gcg aca gct gac cag      1523
Lys Ala Leu Gly Glu Arg Ile Phe Ala Leu Glu Ala Thr Ala Asp Gln
        355                 360                 365 tca gca gct tca ttt gag atg gaa atg tct cag act ggc ttc agt gct      1571
Ser Ala Ala Ser Phe Glu Met Glu Met Ser Gln Thr Gly Phe Ser Ala
370                 375                 380 cac tac tcc cag gac tgg gtc atg ctt gga gcg gtg gga gcc tat gac      1619
His Tyr Ser Gln Asp Trp Val Met Leu Gly Ala Val Gly Ala Tyr Asp
385                 390                 395                 400 tgg aac gga act gtg gtc atg cag aag gct aac cag atg gtc atc cct      1667
Trp Asn Gly Thr Val Val Met Gln Lys Ala Asn Gln Met Val Ile Pro
                405                 410                 415 cat aac acc acc ttt caa act gag ccc gcc aag atg aac gag cct ctg      1715
His Asn Thr Thr Phe Gln Thr Glu Pro Ala Lys Met Asn Glu Pro Leu
            420                 425                 430 gct tct tat tta ggt tac aca gtg aac tcg gcc acc atc cct gga gat      1763
Ala Ser Tyr Leu Gly Tyr Thr Val Asn Ser Ala Thr Ile Pro Gly Asp
        435                 440                 445 gtg ctc tac atc gct ggg cag cct cgg tac aat cat acg ggc cag gtc      1811
Val Leu Tyr Ile Ala Gly Gln Pro Arg Tyr Asn His Thr Gly Gln Val
450                 455                 460 gtc atc tac aag atg gag gat ggg aac atc aac att ctg cag aca ctc      1859
Val Ile Tyr Lys Met Glu Asp Gly Asn Ile Asn Ile Leu Gln Thr Leu
465                 470                 475                 480 ggc gga gag cag att ggt tcc tac ttt ggt agt gtc tta aca aca att      1907
Gly Gly Glu Gln Ile Gly Ser Tyr Phe Gly Ser Val Leu Thr Thr Ile
                485                 490                 495 gac atc gac aaa gat tct tat act gat ctg ctt ctc gtc ggg gcc ccc      1955
Asp Ile Asp Lys Asp Ser Tyr Thr Asp Leu Leu Leu Val Gly Ala Pro
            500                 505                 510 atg tac atg ggg aca gag aaa gag gaa cag ggc aag gtg tac gtg tac      2003
Met Tyr Met Gly Thr Glu Lys Glu Glu Gln Gly Lys Val Tyr Val Tyr
        515                 520                 525 gct gtg aat cag aca agg ttt gaa tat caa atg agc ctg gaa cca att      2051
Ala Val Asn Gln Thr Arg Phe Glu Tyr Gln Met Ser Leu Glu Pro Ile
530                 535                 540 agg cag acc tgc tgc tca tcc ctg aag gat aat tca tgc acg aaa gaa      2099
Arg Gln Thr Cys Cys Ser Ser Leu Lys Asp Asn Ser Cys Thr Lys Glu
545                 550                 555                 560 aac aag aat gag ccc tgc ggg gcc cgc ttc gga aca gca att gct gct      2147
Asn Lys Asn Glu Pro Cys Gly Ala Arg Phe Gly Thr Ala Ile Ala Ala
                565                 570                 575 gta aaa gac ctc aac gtg gat gga ttt aat gac gtc gtg att gga gct      2195
Val Lys Asp Leu Asn Val Asp Gly Phe Asn Asp Val Val Ile Gly Ala
            580                 585                 590 ccg ctg gaa gat gac cac gca gga gct gtg tac att tat cat ggc agt      2243
Pro Leu Glu Asp Asp His Ala Gly Ala Val Tyr Ile Tyr His Gly Ser
        595                 600                 605
```

```
ggc aag acc ata agg gag gcg tat gca caa cgc att cca tca ggt ggg         2291
Gly Lys Thr Ile Arg Glu Ala Tyr Ala Gln Arg Ile Pro Ser Gly Gly
        610             615                 620 gat ggc aag acc ctg aaa ttt ttc ggc cag tct atc cac gga gag atg         2339
Asp Gly Lys Thr Leu Lys Phe Phe Gly Gln Ser Ile His Gly Glu Met
625             630                 635                 640 gat tta aat ggt gac ggt ctg act gac gtg acc att gga ggc ctt ggt         2387
Asp Leu Asn Gly Asp Gly Leu Thr Asp Val Thr Ile Gly Gly Leu Gly
                645                 650                 655 gga gca gcc ctc ttc tgg gcc aga gat gtg gct gta gtt aaa gtg acc         2435
Gly Ala Ala Leu Phe Trp Ala Arg Asp Val Ala Val Val Lys Val Thr
                    660                 665                 670 atg aat ttt gaa ccc aat aaa gtg aat att caa aag aaa aac tgc cgt         2483
Met Asn Phe Glu Pro Asn Lys Val Asn Ile Gln Lys Lys Asn Cys Arg
            675                 680                 685 gtg gag ggc aaa gaa aca gtg tgc ata aat gct aca atg tgt ttt cat         2531
Val Glu Gly Lys Glu Thr Val Cys Ile Asn Ala Thr Met Cys Phe His
        690                 695                 700 gtg aaa tta aag tct aaa gag gac tca att tac gag gct gat ctg cag         2579
Val Lys Leu Lys Ser Lys Glu Asp Ser Ile Tyr Glu Ala Asp Leu Gln
705             710                 715                 720 tac cgt gtc acc ctt gat tca ctg agg cag ata tca cgg agc ttt ttt         2627
Tyr Arg Val Thr Leu Asp Ser Leu Arg Gln Ile Ser Arg Ser Phe Phe
                725                 730                 735 tct gga act cag gaa agg aag att caa aga aat atc acc gtt cga gaa         2675
Ser Gly Thr Gln Glu Arg Lys Ile Gln Arg Asn Ile Thr Val Arg Glu
                    740                 745                 750 tca gaa tgc atc agg cac tcc ttc tac atg ttg gac aaa cat gac ttt         2723
Ser Glu Cys Ile Arg His Ser Phe Tyr Met Leu Asp Lys His Asp Phe
            755                 760                 765 cag gac tct gtg aga gtg act ctg gat ttt aat ctc act gat cca gaa         2771
Gln Asp Ser Val Arg Val Thr Leu Asp Phe Asn Leu Thr Asp Pro Glu
        770                 775                 780 aat ggt cct gta ctt gat gac gct ctg cca aac tca gtc cac gaa cac         2819
Asn Gly Pro Val Leu Asp Asp Ala Leu Pro Asn Ser Val His Glu His
785             790                 795                 800 att ccc ttt gcc aaa gac tgt gga aac aag gaa aga tgc att tca gac         2867
Ile Pro Phe Ala Lys Asp Cys Gly Asn Lys Glu Arg Cys Ile Ser Asp
                805                 810                 815 ctc act ctg aat gtg tcc acc aca gaa aag agc ctg ctg atc gtc aag         2915
Leu Thr Leu Asn Val Ser Thr Thr Glu Lys Ser Leu Leu Ile Val Lys
                    820                 825                 830 tcc cag cat gac aag ttc aac gtt agc ctc acc gtc aaa aac aaa gga         2963
Ser Gln His Asp Lys Phe Asn Val Ser Leu Thr Val Lys Asn Lys Gly
            835                 840                 845 gac agt gcg tac aac acc agg aca gtg gtg cag cat tca cca aat ctg         3011
Asp Ser Ala Tyr Asn Thr Arg Thr Val Val Gln His Ser Pro Asn Leu
        850                 855                 860 att ttt tcg gga att gag gag atc caa aaa gat agc tgt gaa tct aat         3059
Ile Phe Ser Gly Ile Glu Glu Ile Gln Lys Asp Ser Cys Glu Ser Asn
865             870                 875                 880 caa aat atc act tgc aga gtt gga tat cct ttc cta aga gca gga gaa         3107
Gln Asn Ile Thr Cys Arg Val Gly Tyr Pro Phe Leu Arg Ala Gly Glu
                885                 890                 895 acg gtt acc ttc aaa ata ata ttc cag ttt aac aca tcc cat ctc tcg         3155
Thr Val Thr Phe Lys Ile Ile Phe Gln Phe Asn Thr Ser His Leu Ser
                    900                 905                 910 gaa aat gca atc att cac tta agt gca aca agt gac agt gag gag ccc         3203
Glu Asn Ala Ile Ile His Leu Ser Ala Thr Ser Asp Ser Glu Glu Pro
            915                 920                 925
```

```
ctg gaa tct ctt aat gat aat gaa gta aat att tcc atc cca gta aaa      3251
Leu Glu Ser Leu Asn Asp Asn Glu Val Asn Ile Ser Ile Pro Val Lys
            930                 935                 940 tat gaa gtt gga ctg cag ttt tac agt tct gcg agt gaa cat cac att      3299
Tyr Glu Val Gly Leu Gln Phe Tyr Ser Ser Ala Ser Glu His His Ile
945                 950                 955                 960 tca gtc gct gcc aat gag acg atc cct gag ttt att aac tcc act gag      3347
Ser Val Ala Ala Asn Glu Thr Ile Pro Glu Phe Ile Asn Ser Thr Glu
                965                 970                 975 gac att ggg aat gaa att aat gtc ttc tat acg att aga aag agg ggg      3395
Asp Ile Gly Asn Glu Ile Asn Val Phe Tyr Thr Ile Arg Lys Arg Gly
            980                 985                 990 cat ttc cca atg cca gaa ctt cag  ctg tca att tca ttc  ccc aat ttg    3443
His Phe Pro Met Pro Glu Leu Gln  Leu Ser Ile Ser Phe  Pro Asn Leu
        995                 1000                1005 acg gca gat ggt tat cct gta ctg tac cca att gga  tgg tca tct         3488
Thr Ala Asp Gly Tyr Pro Val Leu Tyr Pro Ile Gly  Trp Ser Ser
    1010                1015                    1020 tca gat aat gtg aac tgt aga ccc cgg agc ctt gag  gac ccc ttt         3533
Ser Asp Asn Val Asn Cys Arg Pro Arg Ser Leu Glu  Asp Pro Phe
        1025                1030                1035 ggc atc aac tct ggg aag aaa atg aca ata tcg aag  tct gag gtt         3578
Gly Ile Asn Ser Gly Lys Lys Met Thr Ile Ser Lys  Ser Glu Val
    1040                1045                    1050 ctc aaa aga ggc aca atc cag gac tgc agt agt acg  tgt gga gtt         3623
Leu Lys Arg Gly Thr Ile Gln Asp Cys Ser Ser Thr  Cys Gly Val
    1055                1060                    1065 gcc acc atc acg tgt agc ctc ctt cct tcc gac ctg  agt caa gtg         3668
Ala Thr Ile Thr Cys Ser Leu Leu Pro Ser Asp Leu  Ser Gln Val
    1070                1075                    1080 aat gtc tcg ctc ctc ctg tgg aaa ccg act ttc ata  aga gca cat         3713
Asn Val Ser Leu Leu Leu Trp Lys Pro Thr Phe Ile  Arg Ala His
    1085                1090                    1095 ttt tcc agc tta aac ctt act cta aga gga gaa ctt  aag agt gaa         3758
Phe Ser Ser Leu Asn Leu Thr Leu Arg Gly Glu Leu  Lys Ser Glu
    1100                1105                    1110 aat tca tcg ctg act tta agt agc agc aac cgg aag  cga gag ctg         3803
Asn Ser Ser Leu Thr Leu Ser Ser Ser Asn Arg Lys  Arg Glu Leu
    1115                1120                    1125 gct att cag ata tcc aaa gac ggg ctc cca ggc aga  gtg ccg ctg         3848
Ala Ile Gln Ile Ser Lys Asp Gly Leu Pro Gly Arg  Val Pro Leu
    1130                1135                    1140 tgg gtt atc ctc ctg agc gcc ttc gcg ggg cta ctg  ctg cta atg         3893
Trp Val Ile Leu Leu Ser Ala Phe Ala Gly Leu Leu  Leu Leu Met
    1145                1150                    1155 ctc ctt ata ttg gct ctg tgg aag att gga ttc ttc  aaa agg cca         3938
Leu Leu Ile Leu Ala Leu Trp Lys Ile Gly Phe Phe  Lys Arg Pro
    1160                1165                    1170 ctg aag aag aaa atg gag aaa tgaaggttt catagaaaaa aaaaaaaaa            3989
Leu Lys Lys Lys Met Glu Lys
    1175                1180

<210> SEQ ID NO 2
<211> LENGTH: 1180
<212> TYPE: PRT
<213> ORGANISM: Rattus

<400> SEQUENCE: 2

Met Val Pro Arg Arg Pro Ala Ser Leu Glu Val Thr Val Ala Cys Ile
1               5                   10                  15
```

-continued

Trp Leu Leu Thr Val Ile Leu Gly Phe Cys Val Ser Phe Asn Val Asp
            20                  25              30

Val Lys Asn Ser Met Ser Phe Ser Gly Pro Val Glu Asp Met Phe Gly
            35              40              45

Tyr Thr Val Gln Gln Tyr Glu Asn Glu Glu Gly Lys Trp Val Leu Ile
            50              55              60

Gly Ser Pro Leu Val Gly Gln Pro Lys Ala Arg Thr Gly Asp Val Tyr
 65             70                  75                      80

Lys Cys Pro Val Gly Arg Glu Arg Ala Met Pro Cys Val Lys Leu Asp
                85                  90              95

Leu Pro Val Asn Thr Ser Ile Pro Asn Val Thr Glu Ile Lys Glu Asn
            100             105             110

Met Thr Phe Gly Ser Thr Leu Val Thr Asn Pro Asn Gly Gly Phe Leu
            115             120             125

Ala Cys Gly Pro Leu Tyr Ala Tyr Arg Cys His Leu His Tyr Thr
            130             135             140

Thr Gly Ile Cys Ser Asp Val Ser Pro Thr Phe Gln Val Val Asn Ser
145             150             155                         160

Phe Ala Pro Val Gln Glu Cys Ser Thr Gln Leu Asp Ile Val Ile Val
                165             170             175

Leu Asp Gly Ser Asn Ser Ile Tyr Pro Trp Glu Ser Val Ile Ala Phe
            180             185             190

Leu Asn Asp Leu Leu Lys Arg Met Asp Ile Gly Pro Lys Gln Thr Gln
            195             200             205

Val Gly Ile Val Gln Tyr Gly Glu Asn Val Thr His Glu Phe Asn Leu
            210             215             220

Asn Lys Tyr Ser Ser Thr Glu Glu Val Leu Val Ala Ala Asn Lys Ile
225             230             235                         240

Gly Arg Gln Gly Gly Leu Gln Thr Met Thr Ala Leu Gly Ile Asp Thr
            245             250             255

Ala Arg Lys Glu Ala Phe Thr Glu Ala Arg Gly Ala Arg Arg Gly Val
            260             265             270

Lys Lys Val Met Val Ile Val Thr Asp Gly Glu Ser His Asp Asn Tyr
            275             280             285

Arg Leu Lys Gln Val Ile Gln Asp Cys Glu Asp Glu Asn Ile Gln Arg
            290             295             300

Phe Ser Ile Ala Ile Leu Gly His Tyr Asn Arg Gly Asn Leu Ser Thr
305             310             315                         320

Glu Lys Phe Val Glu Glu Ile Lys Ser Ile Ala Ser Glu Pro Thr Glu
            325             330             335

Lys His Phe Phe Asn Val Ser Asp Glu Leu Ala Leu Val Thr Ile Val
            340             345             350

Lys Ala Leu Gly Glu Arg Ile Phe Ala Leu Glu Ala Thr Ala Asp Gln
            355             360             365

Ser Ala Ala Ser Phe Glu Met Glu Met Ser Gln Thr Gly Phe Ser Ala
            370             375             380

His Tyr Ser Gln Asp Trp Val Met Leu Gly Ala Val Gly Ala Tyr Asp
385             390             395                         400

Trp Asn Gly Thr Val Val Met Gln Lys Ala Asn Gln Met Val Ile Pro
            405             410             415

His Asn Thr Thr Phe Gln Thr Glu Pro Ala Lys Met Asn Glu Pro Leu
            420             425             430

```
Ala Ser Tyr Leu Gly Tyr Thr Val Asn Ser Ala Thr Ile Pro Gly Asp
        435                 440                 445

Val Leu Tyr Ile Ala Gly Gln Pro Arg Tyr Asn His Thr Gly Gln Val
    450                 455                 460

Val Ile Tyr Lys Met Glu Asp Gly Asn Ile Asn Ile Leu Gln Thr Leu
465                 470                 475                 480

Gly Gly Glu Gln Ile Gly Ser Tyr Phe Gly Ser Val Leu Thr Thr Ile
                485                 490                 495

Asp Ile Asp Lys Asp Ser Tyr Thr Asp Leu Leu Val Gly Ala Pro
            500                 505                 510

Met Tyr Met Gly Thr Glu Lys Glu Gln Gly Lys Val Tyr Val Tyr
        515                 520                 525

Ala Val Asn Gln Thr Arg Phe Glu Tyr Gln Met Ser Leu Glu Pro Ile
    530                 535                 540

Arg Gln Thr Cys Cys Ser Ser Leu Lys Asp Asn Ser Cys Thr Lys Glu
545                 550                 555                 560

Asn Lys Asn Glu Pro Cys Gly Ala Arg Phe Gly Thr Ala Ile Ala Ala
                565                 570                 575

Val Lys Asp Leu Asn Val Asp Gly Phe Asn Asp Val Val Ile Gly Ala
            580                 585                 590

Pro Leu Glu Asp Asp His Ala Gly Ala Val Tyr Ile Tyr His Gly Ser
        595                 600                 605

Gly Lys Thr Ile Arg Glu Ala Tyr Ala Gln Arg Ile Pro Ser Gly Gly
    610                 615                 620

Asp Gly Lys Thr Leu Lys Phe Phe Gly Gln Ser Ile His Gly Glu Met
625                 630                 635                 640

Asp Leu Asn Gly Asp Gly Leu Thr Asp Val Thr Ile Gly Gly Leu Gly
                645                 650                 655

Gly Ala Ala Leu Phe Trp Ala Arg Asp Val Ala Val Val Lys Val Thr
            660                 665                 670

Met Asn Phe Glu Pro Asn Lys Val Asn Ile Gln Lys Lys Asn Cys Arg
        675                 680                 685

Val Glu Gly Lys Glu Thr Val Cys Ile Asn Ala Thr Met Cys Phe His
    690                 695                 700

Val Lys Leu Lys Ser Lys Glu Asp Ser Ile Tyr Glu Ala Asp Leu Gln
705                 710                 715                 720

Tyr Arg Val Thr Leu Asp Ser Leu Arg Gln Ile Ser Arg Ser Phe Phe
                725                 730                 735

Ser Gly Thr Gln Glu Arg Lys Ile Gln Arg Asn Ile Thr Val Arg Glu
            740                 745                 750

Ser Glu Cys Ile Arg His Ser Phe Tyr Met Leu Asp Lys His Asp Phe
        755                 760                 765

Gln Asp Ser Val Arg Val Thr Leu Asp Phe Asn Leu Thr Asp Pro Glu
    770                 775                 780

Asn Gly Pro Val Leu Asp Asp Ala Leu Pro Asn Ser Val His Glu His
785                 790                 795                 800

Ile Pro Phe Ala Lys Asp Cys Gly Asn Lys Glu Arg Cys Ile Ser Asp
                805                 810                 815

Leu Thr Leu Asn Val Ser Thr Thr Glu Lys Ser Leu Leu Ile Val Lys
            820                 825                 830

Ser Gln His Asp Lys Phe Asn Val Ser Leu Thr Val Lys Asn Lys Gly
        835                 840                 845

Asp Ser Ala Tyr Asn Thr Arg Thr Val Val Gln His Ser Pro Asn Leu
```

```
            850             855             860
Ile Phe Ser Gly Ile Glu Glu Ile Gln Lys Asp Ser Cys Glu Ser Asn
865                     870                     875             880

Gln Asn Ile Thr Cys Arg Val Gly Tyr Pro Phe Leu Arg Ala Gly Glu
                885                     890                 895

Thr Val Thr Phe Lys Ile Ile Phe Gln Phe Asn Thr Ser His Leu Ser
            900                     905                 910

Glu Asn Ala Ile Ile His Leu Ser Ala Thr Ser Asp Ser Glu Glu Pro
        915                     920                 925

Leu Glu Ser Leu Asn Asp Asn Glu Val Asn Ile Ser Ile Pro Val Lys
    930                     935                 940

Tyr Glu Val Gly Leu Gln Phe Tyr Ser Ser Ala Ser Glu His His Ile
945                     950                     955             960

Ser Val Ala Ala Asn Glu Thr Ile Pro Glu Phe Ile Asn Ser Thr Glu
                965                     970                 975

Asp Ile Gly Asn Glu Ile Asn Val Phe Tyr Thr Ile Arg Lys Arg Gly
                980                     985                 990

His Phe Pro Met Pro Glu Leu Gln Leu Ser Ile Ser Phe Pro Asn Leu
            995                 1000                1005

Thr Ala Asp Gly Tyr Pro Val Leu Tyr Pro Ile Gly Trp Ser Ser
    1010                1015                1020

Ser Asp Asn Val Asn Cys Arg Pro Arg Ser Leu Glu Asp Pro Phe
    1025                1030                1035

Gly Ile Asn Ser Gly Lys Lys Met Thr Ile Ser Lys Ser Glu Val
    1040                1045                1050

Leu Lys Arg Gly Thr Ile Gln Asp Cys Ser Ser Thr Cys Gly Val
    1055                1060                1065

Ala Thr Ile Thr Cys Ser Leu Leu Pro Ser Asp Leu Ser Gln Val
    1070                1075                1080

Asn Val Ser Leu Leu Leu Trp Lys Pro Thr Phe Ile Arg Ala His
    1085                1090                1095

Phe Ser Ser Leu Asn Leu Thr Leu Arg Gly Glu Leu Lys Ser Glu
    1100                1105                1110

Asn Ser Ser Leu Thr Leu Ser Ser Ser Asn Arg Lys Arg Glu Leu
    1115                1120                1125

Ala Ile Gln Ile Ser Lys Asp Gly Leu Pro Gly Arg Val Pro Leu
    1130                1135                1140

Trp Val Ile Leu Leu Ser Ala Phe Ala Gly Leu Leu Leu Leu Met
    1145                1150                1155

Leu Leu Ile Leu Ala Leu Trp Lys Ile Gly Phe Phe Lys Arg Pro
    1160                1165                1170

Leu Lys Lys Lys Met Glu Lys
    1175                1180

<210> SEQ ID NO 3
<211> LENGTH: 5373
<212> TYPE: DNA
<213> ORGANISM: Homo sapiens
<220> FEATURE:
<221> NAME/KEY: CDS
<222> LOCATION: (49)..(3591)
<223> OTHER INFORMATION:

<400> SEQUENCE: 3
gaattcctgc aaacccagcg caactacggt cccccggtca gacccagg atg ggg cca      57
                                                    Met Gly Pro
```

-continued

```
                              1
gaa cgg aca ggg gcc gcg ccg ctg ccg ctg ctg ctg gtg tta gcg ctc         105
Glu Arg Thr Gly Ala Ala Pro Leu Pro Leu Leu Leu Val Leu Ala Leu
    5                   10                  15 agt caa ggc att tta aat tgt tgt ttg gcc tac aat gtt ggt ctc cca         153
Ser Gln Gly Ile Leu Asn Cys Cys Leu Ala Tyr Asn Val Gly Leu Pro
20                  25                  30                  35 gaa gca aaa ata ttt tcc ggt cct tca agt gaa cag ttt ggg tat gca         201
Glu Ala Lys Ile Phe Ser Gly Pro Ser Ser Glu Gln Phe Gly Tyr Ala
                40                  45                  50 gtg cag cag ttt ata aat cca aaa ggc aac tgg tta ctg gtt ggt tca         249
Val Gln Gln Phe Ile Asn Pro Lys Gly Asn Trp Leu Leu Val Gly Ser
            55                  60                  65 ccc tgg agt ggc ttt cct gag aac cga atg gga gat gtg tat aaa tgt         297
Pro Trp Ser Gly Phe Pro Glu Asn Arg Met Gly Asp Val Tyr Lys Cys
        70                  75                  80 cct gtt gac cta tcc act gcc aca tgt gaa aaa cta aat ttg caa act         345
Pro Val Asp Leu Ser Thr Ala Thr Cys Glu Lys Leu Asn Leu Gln Thr
    85                  90                  95 tca aca agc att cca aat gtt act gag atg aaa acc aac atg agc ctc         393
Ser Thr Ser Ile Pro Asn Val Thr Glu Met Lys Thr Asn Met Ser Leu
100                 105                 110                 115 ggc ttg atc ctc acc agg aac atg gga act gga ggt ttt ctc aca tgt         441
Gly Leu Ile Leu Thr Arg Asn Met Gly Thr Gly Gly Phe Leu Thr Cys
                120                 125                 130 ggt cct ctg tgg gca cag caa tgt ggg aat cag tat tac aca acg ggt         489
Gly Pro Leu Trp Ala Gln Gln Cys Gly Asn Gln Tyr Tyr Thr Thr Gly
            135                 140                 145 gtg tgt tct gac atc agt cct gat ttt cag ctc tca gcc agc ttc tca         537
Val Cys Ser Asp Ile Ser Pro Asp Phe Gln Leu Ser Ala Ser Phe Ser
        150                 155                 160 cct gca act cag ccc tgc cct tcc ctc ata gat gtt gtg gtt gtg tgt         585
Pro Ala Thr Gln Pro Cys Pro Ser Leu Ile Asp Val Val Val Val Cys
    165                 170                 175 gat gaa tca aat agt att tat cct tgg gat gca gta aag aat ttt ttg         633
Asp Glu Ser Asn Ser Ile Tyr Pro Trp Asp Ala Val Lys Asn Phe Leu
180                 185                 190                 195 gaa aaa ttt gta caa ggc ctt gat ata ggc ccc aca aag aca cag gtg         681
Glu Lys Phe Val Gln Gly Leu Asp Ile Gly Pro Thr Lys Thr Gln Val
                200                 205                 210 ggg tta att cag tat gcc aat aat cca aga gtt gtg ttt aac ttg aac         729
Gly Leu Ile Gln Tyr Ala Asn Asn Pro Arg Val Val Phe Asn Leu Asn
            215                 220                 225 aca tat aaa acc aaa gaa gaa atg att gta gca aca tcc cag aca tcc         777
Thr Tyr Lys Thr Lys Glu Glu Met Ile Val Ala Thr Ser Gln Thr Ser
        230                 235                 240 caa tat ggt ggg gac ctc aca aac aca ttc gga gca att caa tat gca         825
Gln Tyr Gly Gly Asp Leu Thr Asn Thr Phe Gly Ala Ile Gln Tyr Ala
    245                 250                 255 aga aaa tat gcc tat tca gca gct tct ggt ggg cga cga agt gct acg         873
Arg Lys Tyr Ala Tyr Ser Ala Ala Ser Gly Gly Arg Arg Ser Ala Thr
260                 265                 270                 275 aaa gta atg gta gtt gta act gac ggt gaa tca cat gat ggt tca atg         921
Lys Val Met Val Val Val Thr Asp Gly Glu Ser His Asp Gly Ser Met
                280                 285                 290 ttg aaa gct gtg att gat caa tgc aac cat gac aat ata ctg agg ttt         969
Leu Lys Ala Val Ile Asp Gln Cys Asn His Asp Asn Ile Leu Arg Phe
            295                 300                 305 ggc ata gca gtt ctt ggg tac tta aac aga aac gcc ctt gat act aaa        1017
```

```
                                                                    -continued Gly Ile Ala Val Leu Gly Tyr Leu Asn Arg Asn Ala Leu Asp Thr Lys
        310                 315                 320 aat tta ata aaa gaa ata aaa gcg atc gct agt att cca aca gaa aga        1065
Asn Leu Ile Lys Glu Ile Lys Ala Ile Ala Ser Ile Pro Thr Glu Arg
325                 330                 335 tac ttt ttc aat gtg tct gat gaa gca gct cta cta gaa aag gct ggg        1113
Tyr Phe Phe Asn Val Ser Asp Glu Ala Ala Leu Leu Glu Lys Ala Gly
340                 345                 350                 355 aca tta gga gaa caa att ttc agc att gaa ggt act gtt caa gga gga        1161
Thr Leu Gly Glu Gln Ile Phe Ser Ile Glu Gly Thr Val Gln Gly Gly
                360                 365                 370 gac aac ttt cag atg gaa atg tca caa gtg gga ttc agt gca gat tac        1209
Asp Asn Phe Gln Met Glu Met Ser Gln Val Gly Phe Ser Ala Asp Tyr
            375                 380                 385 tct tct caa aat gat att ctg atg ctg ggt gca gtg gga gct ttt ggc        1257
Ser Ser Gln Asn Asp Ile Leu Met Leu Gly Ala Val Gly Ala Phe Gly
        390                 395                 400 tgg agt ggg acc att gtc cag aag aca tct cat ggc cat ttg atc ttt        1305
Trp Ser Gly Thr Ile Val Gln Lys Thr Ser His Gly His Leu Ile Phe
    405                 410                 415 cct aaa caa gcc ttt gac caa att ctg cag gac aga aat cac agt tca        1353
Pro Lys Gln Ala Phe Asp Gln Ile Leu Gln Asp Arg Asn His Ser Ser
420                 425                 430                 435 tat tta ggt tac tct gtg gct gca att tct act gga gaa agc act cac        1401
Tyr Leu Gly Tyr Ser Val Ala Ala Ile Ser Thr Gly Glu Ser Thr His
                440                 445                 450 ttt gtt gct ggt gct cct cgg gca aat tat acc ggc cag ata gtg cta        1449
Phe Val Ala Gly Ala Pro Arg Ala Asn Tyr Thr Gly Gln Ile Val Leu
            455                 460                 465 tat agt gtg aat gag aat ggc aat atc acg gtt att cag gct cac cga        1497
Tyr Ser Val Asn Glu Asn Gly Asn Ile Thr Val Ile Gln Ala His Arg
        470                 475                 480 ggt gac cag att ggc tcc tat ttt ggt agt gtg ctg tgt tca gtt gat        1545
Gly Asp Gln Ile Gly Ser Tyr Phe Gly Ser Val Leu Cys Ser Val Asp
    485                 490                 495 gtg gat aaa gac acc att aca gac gtg ctc ttg gta ggt gca cca atg        1593
Val Asp Lys Asp Thr Ile Thr Asp Val Leu Leu Val Gly Ala Pro Met
500                 505                 510                 515 tac atg agt gac cta aag aaa gag gaa gga aga gtc tac ctg ttt act        1641
Tyr Met Ser Asp Leu Lys Lys Glu Glu Gly Arg Val Tyr Leu Phe Thr
                520                 525                 530 atc aaa aag ggc att ttg ggt cag cac caa ttt ctt gaa ggc ccc gag        1689
Ile Lys Lys Gly Ile Leu Gly Gln His Gln Phe Leu Glu Gly Pro Glu
            535                 540                 545 ggc att gaa aac act cga ttt ggt tca gca att gca gct ctt tca gac        1737
Gly Ile Glu Asn Thr Arg Phe Gly Ser Ala Ile Ala Ala Leu Ser Asp
        550                 555                 560 atc aac atg gat ggc ttt aat gat gtg att gtt ggt tca cca cta gaa        1785
Ile Asn Met Asp Gly Phe Asn Asp Val Ile Val Gly Ser Pro Leu Glu
    565                 570                 575 aat cag aat tct gga gct gta tac att tac aat ggt cat cag ggc act        1833
Asn Gln Asn Ser Gly Ala Val Tyr Ile Tyr Asn Gly His Gln Gly Thr
580                 585                 590                 595 atc cgc aca aag tat tcc cag aaa atc ttg gga tcc gat gga gcc ttt        1881
Ile Arg Thr Lys Tyr Ser Gln Lys Ile Leu Gly Ser Asp Gly Ala Phe
                600                 605                 610 agg agc cat ctc cag tac ttt ggg agg tcc ttg gat ggc tat gga gat        1929
Arg Ser His Leu Gln Tyr Phe Gly Arg Ser Leu Asp Gly Tyr Gly Asp
            615                 620                 625
```

-continued

| | |
|---|---|
| tta aat ggg gat tcc atc acc gat gtg tct att ggt gcc ttt gga caa<br>Leu Asn Gly Asp Ser Ile Thr Asp Val Ser Ile Gly Ala Phe Gly Gln<br>630                        635                        640 | 1977 |
| gtg gtt caa ctc tgg tca caa agt att gct gat gta gct ata gaa gct<br>Val Val Gln Leu Trp Ser Gln Ser Ile Ala Asp Val Ala Ile Glu Ala<br>645                        650                        655 | 2025 |
| tca ttc aca cca gaa aaa atc act ttg gtc aac aag aat gct cag ata<br>Ser Phe Thr Pro Glu Lys Ile Thr Leu Val Asn Lys Asn Ala Gln Ile<br>660                        665                        670                        675 | 2073 |
| att ctc aaa ctc tgc ttc agt gca aag ttc aga cct act aag caa aac<br>Ile Leu Lys Leu Cys Phe Ser Ala Lys Phe Arg Pro Thr Lys Gln Asn<br>                        680                        685                        690 | 2121 |
| aat caa gtg gcc att gta tat aac atc aca ctt gat gca gat gga ttt<br>Asn Gln Val Ala Ile Val Tyr Asn Ile Thr Leu Asp Ala Asp Gly Phe<br>                        695                        700                        705 | 2169 |
| tca tcc aga gta acc tcc agg ggg tta ttt aaa gaa aac aat gaa agg<br>Ser Ser Arg Val Thr Ser Arg Gly Leu Phe Lys Glu Asn Asn Glu Arg<br>          710                        715                        720 | 2217 |
| tgc ctg cag aag aat atg gta gta aat caa gca cag agt tgc ccc gag<br>Cys Leu Gln Lys Asn Met Val Val Asn Gln Ala Gln Ser Cys Pro Glu<br>725                        730                        735 | 2265 |
| cac atc att tat ata cag gag ccc tct gat gtt gtc aac tct ttg gat<br>His Ile Ile Tyr Ile Gln Glu Pro Ser Asp Val Val Asn Ser Leu Asp<br>740                        745                        750                        755 | 2313 |
| ttg cgt gtg gac atc agt ctg gaa aac cct ggc act agc cct gcc ctt<br>Leu Arg Val Asp Ile Ser Leu Glu Asn Pro Gly Thr Ser Pro Ala Leu<br>                        760                        765                        770 | 2361 |
| gaa gcc tat tct gag act gcc aag gtc ttc agt att cct ttc cac aaa<br>Glu Ala Tyr Ser Glu Thr Ala Lys Val Phe Ser Ile Pro Phe His Lys<br>          775                        780                        785 | 2409 |
| gac tgt ggt gag gat gga ctt tgc att tct gat cta gtc cta gat gtc<br>Asp Cys Gly Glu Asp Gly Leu Cys Ile Ser Asp Leu Val Leu Asp Val<br>790                        795                        800 | 2457 |
| cga caa ata cca gct gct caa gaa caa ccc ttt att gtc agc aac caa<br>Arg Gln Ile Pro Ala Ala Gln Glu Gln Pro Phe Ile Val Ser Asn Gln<br>805                        810                        815 | 2505 |
| aac aaa agg tta aca ttt tca gta aca ctg aaa aat aaa agg gaa agt<br>Asn Lys Arg Leu Thr Phe Ser Val Thr Leu Lys Asn Lys Arg Glu Ser<br>820                        825                        830                        835 | 2553 |
| gca tac aac act gga att gtt gtt gat ttt tca gaa aac ttg ttt ttt<br>Ala Tyr Asn Thr Gly Ile Val Val Asp Phe Ser Glu Asn Leu Phe Phe<br>                        840                        845                        850 | 2601 |
| gca tca ttc tcc cta ccg gtt gat ggg aca gaa gta aca tgc cag gtg<br>Ala Ser Phe Ser Leu Pro Val Asp Gly Thr Glu Val Thr Cys Gln Val<br>          855                        860                        865 | 2649 |
| gct gca tct cag aag tct gtt gcc tgc gat gta ggc tac cct gct tta<br>Ala Ala Ser Gln Lys Ser Val Ala Cys Asp Val Gly Tyr Pro Ala Leu<br>870                        875                        880 | 2697 |
| aag aga gaa caa cag gtg act ttt act att aac ttt gac ttc aat ctt<br>Lys Arg Glu Gln Gln Val Thr Phe Thr Ile Asn Phe Asp Phe Asn Leu<br>885                        890                        895 | 2745 |
| caa aac ctt cag aat cag gcg tct ctc agt ttc caa gcc tta agt gaa<br>Gln Asn Leu Gln Asn Gln Ala Ser Leu Ser Phe Gln Ala Leu Ser Glu<br>900                        905                        910                        915 | 2793 |
| agc caa gaa gaa aac aag gct gat aat ttg gtc aac ctc aaa att cct<br>Ser Gln Glu Glu Asn Lys Ala Asp Asn Leu Val Asn Leu Lys Ile Pro<br>                        920                        925                        930 | 2841 |
| ctc ctg tat gat gct gaa att cac tta aca aga tct acc aac ata aat<br>Leu Leu Tyr Asp Ala Glu Ile His Leu Thr Arg Ser Thr Asn Ile Asn<br>          935                        940                        945 | 2889 |

| | | |
|---|---|---|
| ttt tat gaa atc tct tcg gat ggg aat gtt cct tca atc gtg cac agt<br>Phe Tyr Glu Ile Ser Ser Asp Gly Asn Val Pro Ser Ile Val His Ser<br>950 955 960 | | 2937 |
| ttt gaa gat gtt ggt cca aaa ttc atc ttc tcc ctg aag gta aca aca<br>Phe Glu Asp Val Gly Pro Lys Phe Ile Phe Ser Leu Lys Val Thr Thr<br>965 970 975 | | 2985 |
| gga agt gtt cca gta agc atg gca act gta atc atc cac atc cct cag<br>Gly Ser Val Pro Val Ser Met Ala Thr Val Ile Ile His Ile Pro Gln<br>980 985 990 995 | | 3033 |
| tat acc aaa gaa aag aac cca ctg atg tac cta act ggg gtg caa<br>Tyr Thr Lys Glu Lys Asn Pro Leu Met Tyr Leu Thr Gly Val Gln<br>1000 1005 1010 | | 3078 |
| aca gac aag gct ggt gac atc agt tgt aat gca gat atc aat cca<br>Thr Asp Lys Ala Gly Asp Ile Ser Cys Asn Ala Asp Ile Asn Pro<br>1015 1020 1025 | | 3123 |
| ctg aaa ata gga caa aca tct tct tct gta tct ttc aaa agt gaa<br>Leu Lys Ile Gly Gln Thr Ser Ser Ser Val Ser Phe Lys Ser Glu<br>1030 1035 1040 | | 3168 |
| aat ttc agg cac acc aaa gaa ttg aac tgc aga act gct tcc tgt<br>Asn Phe Arg His Thr Lys Glu Leu Asn Cys Arg Thr Ala Ser Cys<br>1045 1050 1055 | | 3213 |
| agt aat gtt acc tgc tgg ttg aaa gac gtt cac atg aaa gga gaa<br>Ser Asn Val Thr Cys Trp Leu Lys Asp Val His Met Lys Gly Glu<br>1060 1065 1070 | | 3258 |
| tac ttt gtt aat gtg act acc aga att tgg aac ggg act ttc gca<br>Tyr Phe Val Asn Val Thr Thr Arg Ile Trp Asn Gly Thr Phe Ala<br>1075 1080 1085 | | 3303 |
| tca tca acg ttc cag aca gta cag cta acg gca gct gca gaa atc<br>Ser Ser Thr Phe Gln Thr Val Gln Leu Thr Ala Ala Ala Glu Ile<br>1090 1095 1100 | | 3348 |
| aac acc tat aac cct gag ata tat gtg att gaa gat aac act gtt<br>Asn Thr Tyr Asn Pro Glu Ile Tyr Val Ile Glu Asp Asn Thr Val<br>1105 1110 1115 | | 3393 |
| acg att ccc ctg atg ata atg aaa cct gat gag aaa gcc gaa gta<br>Thr Ile Pro Leu Met Ile Met Lys Pro Asp Glu Lys Ala Glu Val<br>1120 1125 1130 | | 3438 |
| cca aca gga gtt ata ata gga agt ata att gct gga atc ctt ttg<br>Pro Thr Gly Val Ile Ile Gly Ser Ile Ile Ala Gly Ile Leu Leu<br>1135 1140 1145 | | 3483 |
| ctg tta gct ctg gtt gca att tta tgg aag ctc ggc ttc ttc aaa<br>Leu Leu Ala Leu Val Ala Ile Leu Trp Lys Leu Gly Phe Phe Lys<br>1150 1155 1160 | | 3528 |
| aga aaa tat gaa aag atg acc aaa aat cca gat gag att gat gag<br>Arg Lys Tyr Glu Lys Met Thr Lys Asn Pro Asp Glu Ile Asp Glu<br>1165 1170 1175 | | 3573 |
| acc aca gag ctc agt agc tgaaccagca gacctacctg cagtgggaac<br>Thr Thr Glu Leu Ser Ser<br>1180 | | 3621 |
| cggcagcatc ccagccaggg tttgctgttt gcgtgcatgg atttctttt aaatcccata | | 3681 |
| tttttttat catgtcgtag gtaaactaac ctggtatttt aagagaaaac tgcaggtcag | | 3741 |
| tttggatgaa gaaattgtgg ggggtggggg aggtgcgggg ggcaggtagg gaaataatag | | 3801 |
| ggaaaatacc tattttatat gatgggggaa aaaagtaat ctttaaactg gctggcccag | | 3861 |
| agtttacatt ctaatttgca ttgtgtcaga aacatgaaat gcttccaagc atgacaactt | | 3921 |
| ttaaagaaaa atatgatact ctcgattttt aaggggaaa actgttctct ttaaatatt | | 3981 |
| tgtctttaaa cagcaactac agaagtggaa gtgcttgata tgtaagtact tccacttgtg | | 4041 |

-continued

```
tatattttaa tgaatattga tgttaacaag aggggaaaac aaaacacagg ttttttcaat      4101
ttatgctgct catccaaagt tgccacagat gatacttcca agtgataatt ttatttataa      4161
actaggtaaa atttgttgtt ggttcctttt ataccacggc tgccccttcc acacccatc      4221 ttgctctaat gatcaaaaca tgcttgaata actgagctta gagtatacct cctatatgtc      4281
catttaagtt aggagagggg gcgatataga gactaaggca caaaattttg tttaaaactc      4341
agaatataac atttatgtaa aatcccatct gctagaagcc catcctgtgc cagaggaagg      4401
aaaaggagga aatttccttt ctcttttagg aggcacaaca gttctcttct aggatttgtt      4461
tggctgactg gcagtaacct agtgaatttt tgaaagatga gtaatttctt tggcaacctt      4521
cctcctccct tactgaacca ctctcccacc tcctggtggt accattatta tagaagccct      4581
ctacagcctg actttctctc cagcggtcca aagttatccc ctcctttacc cctcatccaa      4641
agttcccact ccttcaggac agctgctgtg cattagatat tagggggggaa agtcatctgt      4701 ttaatttaca cacttgcatg aattactgta tataaactcc ttaacttcag ggagctattt      4761
tcatttagtg ctaaacaagt aagaaaaata agctagagtg aatttctaaa tgttggaatg      4821
ttatgggatg taaacaatgt aaagtaaaac actctcagga tttcaccaga agttacagat      4881
gaggcactgg aaaccaccac caaattagca ggtgcacctt ctgtggctgt cttgtttctg      4941
aagtactttt tcttccacaa gagtgaattt gacctaggca agtttgttca aaaggtagat      5001
cctgagatga tttggtcaga ttgggataag gcccagcaat ctgcatttta acaagcaccc      5061
cagtcactag gatgcagatg gaccacactt tgagaaacac cacccatttc tacttttgc      5121 accttatttt ctctgttcct gagcccccac attctctagg agaaacttag attaaaattc      5181
acagacacta catatctaaa gctttgacaa gtccttgacc tctataaact tcagagtcct      5241
cattataaaa tgggaagact gagctggagt tcagcagtga tgcttttag ttttaaaagt      5301 ctatgatctg atctggactt cctataatac aaatacacaa tcctccaaga atttgacttg      5361
gaaaaggaat tc                                                          5373
```

<210> SEQ ID NO 4
<211> LENGTH: 1181
<212> TYPE: PRT
<213> ORGANISM: Homo sapiens

<400> SEQUENCE: 4

```
Met Gly Pro Glu Arg Thr Gly Ala Ala Pro Leu Pro Leu Leu Leu Val
1               5                   10                  15

Leu Ala Leu Ser Gln Gly Ile Leu Asn Cys Cys Leu Ala Tyr Asn Val
                20                  25                  30

Gly Leu Pro Glu Ala Lys Ile Phe Ser Gly Pro Ser Glu Gln Phe
                35                  40                  45

Gly Tyr Ala Val Gln Gln Phe Ile Asn Pro Lys Gly Asn Trp Leu Leu
        50                  55                  60

Val Gly Ser Pro Trp Ser Gly Phe Pro Glu Asn Arg Met Gly Asp Val
65                  70                  75                  80

Tyr Lys Cys Pro Val Asp Leu Ser Thr Ala Thr Cys Glu Lys Leu Asn
                85                  90                  95

Leu Gln Thr Ser Thr Ser Ile Pro Asn Val Thr Glu Met Lys Thr Asn
                100                 105                 110

Met Ser Leu Gly Leu Ile Leu Thr Arg Asn Met Gly Thr Gly Gly Phe
        115                 120                 125

Leu Thr Cys Gly Pro Leu Trp Ala Gln Gln Cys Gly Asn Gln Tyr Tyr
```

-continued

```
            130                 135                 140
Thr Thr Gly Val Cys Ser Asp Ile Ser Pro Asp Phe Gln Leu Ser Ala
145                 150                 155                 160

Ser Phe Ser Pro Ala Thr Gln Pro Cys Pro Ser Leu Ile Asp Val Val
                165                 170                 175

Val Val Cys Asp Glu Ser Asn Ser Ile Tyr Pro Trp Asp Ala Val Lys
                180                 185                 190

Asn Phe Leu Glu Lys Phe Val Gln Gly Leu Asp Ile Gly Pro Thr Lys
                195                 200                 205

Thr Gln Val Gly Leu Ile Gln Tyr Ala Asn Asn Pro Arg Val Val Phe
            210                 215                 220

Asn Leu Asn Thr Tyr Lys Thr Lys Glu Glu Met Ile Val Ala Thr Ser
225                 230                 235                 240

Gln Thr Ser Gln Tyr Gly Gly Asp Leu Thr Asn Thr Phe Gly Ala Ile
                245                 250                 255

Gln Tyr Ala Arg Lys Tyr Ala Tyr Ser Ala Ala Ser Gly Gly Arg Arg
                260                 265                 270

Ser Ala Thr Lys Val Met Val Val Val Thr Asp Gly Glu Ser His Asp
            275                 280                 285

Gly Ser Met Leu Lys Ala Val Ile Asp Gln Cys Asn His Asp Asn Ile
290                 295                 300

Leu Arg Phe Gly Ile Ala Val Leu Gly Tyr Leu Asn Arg Asn Ala Leu
305                 310                 315                 320

Asp Thr Lys Asn Leu Ile Lys Glu Ile Lys Ala Ile Ala Ser Ile Pro
                325                 330                 335

Thr Glu Arg Tyr Phe Phe Asn Val Ser Asp Glu Ala Ala Leu Leu Glu
                340                 345                 350

Lys Ala Gly Thr Leu Gly Glu Gln Ile Phe Ser Ile Glu Gly Thr Val
                355                 360                 365

Gln Gly Gly Asp Asn Phe Gln Met Glu Met Ser Gln Val Gly Phe Ser
            370                 375                 380

Ala Asp Tyr Ser Ser Gln Asn Asp Ile Leu Met Leu Gly Ala Val Gly
385                 390                 395                 400

Ala Phe Gly Trp Ser Gly Thr Ile Val Gln Lys Thr Ser His Gly His
                405                 410                 415

Leu Ile Phe Pro Lys Gln Ala Phe Asp Gln Ile Leu Gln Asp Arg Asn
                420                 425                 430

His Ser Ser Tyr Leu Gly Tyr Ser Val Ala Ala Ile Ser Thr Gly Glu
            435                 440                 445

Ser Thr His Phe Val Ala Gly Ala Pro Arg Ala Asn Tyr Thr Gly Gln
            450                 455                 460

Ile Val Leu Tyr Ser Val Asn Glu Asn Gly Asn Ile Thr Val Ile Gln
465                 470                 475                 480

Ala His Arg Gly Asp Gln Ile Gly Ser Tyr Phe Gly Ser Val Leu Cys
                485                 490                 495

Ser Val Asp Val Asp Lys Asp Thr Ile Thr Asp Val Leu Leu Val Gly
                500                 505                 510

Ala Pro Met Tyr Met Ser Asp Leu Lys Lys Glu Glu Gly Arg Val Tyr
                515                 520                 525

Leu Phe Thr Ile Lys Lys Gly Ile Leu Gly Gln His Gln Phe Leu Glu
            530                 535                 540

Gly Pro Glu Gly Ile Glu Asn Thr Arg Phe Gly Ser Ala Ile Ala Ala
545                 550                 555                 560
```

```
Leu Ser Asp Ile Asn Met Asp Gly Phe Asn Asp Val Ile Val Gly Ser
                565                 570                 575

Pro Leu Glu Asn Gln Asn Ser Gly Ala Val Tyr Ile Tyr Asn Gly His
            580                 585                 590

Gln Gly Thr Ile Arg Thr Lys Tyr Ser Gln Lys Ile Leu Gly Ser Asp
        595                 600                 605

Gly Ala Phe Arg Ser His Leu Gln Tyr Phe Gly Arg Ser Leu Asp Gly
    610                 615                 620

Tyr Gly Asp Leu Asn Gly Asp Ser Ile Thr Asp Val Ser Ile Gly Ala
625                 630                 635                 640

Phe Gly Gln Val Val Gln Leu Trp Ser Gln Ser Ile Ala Asp Val Ala
                645                 650                 655

Ile Glu Ala Ser Phe Thr Pro Glu Lys Ile Thr Leu Val Asn Lys Asn
            660                 665                 670

Ala Gln Ile Ile Leu Lys Leu Cys Phe Ser Ala Lys Phe Arg Pro Thr
        675                 680                 685

Lys Gln Asn Asn Gln Val Ala Ile Val Tyr Asn Ile Thr Leu Asp Ala
    690                 695                 700

Asp Gly Phe Ser Ser Arg Val Thr Ser Arg Gly Leu Phe Lys Glu Asn
705                 710                 715                 720

Asn Glu Arg Cys Leu Gln Lys Asn Met Val Val Asn Gln Ala Gln Ser
                725                 730                 735

Cys Pro Glu His Ile Ile Tyr Ile Gln Glu Pro Ser Asp Val Val Asn
            740                 745                 750

Ser Leu Asp Leu Arg Val Asp Ile Ser Leu Glu Asn Pro Gly Thr Ser
        755                 760                 765

Pro Ala Leu Glu Ala Tyr Ser Glu Thr Ala Lys Val Phe Ser Ile Pro
    770                 775                 780

Phe His Lys Asp Cys Gly Glu Asp Gly Leu Cys Ile Ser Asp Leu Val
785                 790                 795                 800

Leu Asp Val Arg Gln Ile Pro Ala Ala Gln Glu Gln Pro Phe Ile Val
                805                 810                 815

Ser Asn Gln Asn Lys Arg Leu Thr Phe Ser Val Thr Leu Lys Asn Lys
            820                 825                 830

Arg Glu Ser Ala Tyr Asn Thr Gly Ile Val Val Asp Phe Ser Glu Asn
        835                 840                 845

Leu Phe Phe Ala Ser Phe Ser Leu Pro Val Asp Gly Thr Glu Val Thr
    850                 855                 860

Cys Gln Val Ala Ala Ser Gln Lys Ser Val Ala Cys Asp Val Gly Tyr
865                 870                 875                 880

Pro Ala Leu Lys Arg Glu Gln Gln Val Thr Phe Thr Ile Asn Phe Asp
                885                 890                 895

Phe Asn Leu Gln Asn Leu Gln Asn Gln Ala Ser Leu Ser Phe Gln Ala
            900                 905                 910

Leu Ser Glu Ser Gln Glu Glu Asn Lys Ala Asp Asn Leu Val Asn Leu
        915                 920                 925

Lys Ile Pro Leu Leu Tyr Asp Ala Glu Ile His Leu Thr Arg Ser Thr
    930                 935                 940

Asn Ile Asn Phe Tyr Glu Ile Ser Ser Asp Gly Asn Val Pro Ser Ile
945                 950                 955                 960

Val His Ser Phe Glu Asp Val Gly Pro Lys Phe Ile Phe Ser Leu Lys
                965                 970                 975
```

-continued

```
Val Thr Thr Gly Ser Val Pro Val Ser Met Ala Thr Val Ile Ile His
                980             985                 990

Ile Pro Gln Tyr Thr Lys Glu Lys Asn Pro Leu Met Tyr Leu Thr Gly
        995                 1000                1005

Val Gln Thr Asp Lys Ala Gly Asp Ile Ser Cys Asn Ala Asp Ile
    1010                1015                1020

Asn Pro Leu Lys Ile Gly Gln Thr Ser Ser Val Ser Phe Lys
    1025                1030                1035

Ser Glu Asn Phe Arg His Thr Lys Glu Leu Asn Cys Arg Thr Ala
    1040                1045                1050

Ser Cys Ser Asn Val Thr Cys Trp Leu Lys Asp Val His Met Lys
    1055                1060                1065

Gly Glu Tyr Phe Val Asn Val Thr Thr Arg Ile Trp Asn Gly Thr
    1070                1075                1080

Phe Ala Ser Ser Thr Phe Gln Thr Val Gln Leu Thr Ala Ala Ala
    1085                1090                1095

Glu Ile Asn Thr Tyr Asn Pro Glu Ile Tyr Val Ile Glu Asp Asn
    1100                1105                1110

Thr Val Thr Ile Pro Leu Met Ile Met Lys Pro Asp Glu Lys Ala
    1115                1120                1125

Glu Val Pro Thr Gly Val Ile Ile Gly Ser Ile Ala Gly Ile
    1130                1135                1140

Leu Leu Leu Leu Ala Leu Val Ala Ile Leu Trp Lys Leu Gly Phe
    1145                1150                1155

Phe Lys Arg Lys Tyr Glu Lys Met Thr Lys Asn Pro Asp Glu Ile
    1160                1165                1170

Asp Glu Thr Thr Glu Leu Ser Ser
    1175                1180

<210> SEQ ID NO 5
<211> LENGTH: 20
<212> TYPE: DNA
<213> ORGANISM: Artificial Sequence
<220> FEATURE:
<223> OTHER INFORMATION: Synthetic probe

<400> SEQUENCE: 5
ccagagtcac tctcacagag                                              20

<210> SEQ ID NO 6
<211> LENGTH: 19
<212> TYPE: DNA
<213> ORGANISM: Artificial Sequence
<220> FEATURE:
<223> OTHER INFORMATION: Synthetic probe

<400> SEQUENCE: 6
cacagcgtac acgtacacc                                               19

<210> SEQ ID NO 7
<211> LENGTH: 19
<212> TYPE: DNA
<213> ORGANISM: Artificial Sequence
<220> FEATURE:
<223> OTHER INFORMATION: Synthetic probe

<400> SEQUENCE: 7
cacttataga catctccag                                               19
```

```
<210> SEQ ID NO 8
<211> LENGTH: 18
<212> TYPE: DNA
<213> ORGANISM: Artificial Sequence
<220> FEATURE:
<223> OTHER INFORMATION: Synthetic probe

<400> SEQUENCE: 8
catccatgtt gatgtctg                                           18

<210> SEQ ID NO 9
<211> LENGTH: 18
<212> TYPE: DNA
<213> ORGANISM: Artificial Sequence
<220> FEATURE:
<223> OTHER INFORMATION: Synthetic probe

<400> SEQUENCE: 9
catgtgattc accgtcag                                           18

<210> SEQ ID NO 10
<211> LENGTH: 24
<212> TYPE: DNA
<213> ORGANISM: Artificial Sequence
<220> FEATURE:
<223> OTHER INFORMATION: Synthetic probe

<400> SEQUENCE: 10
gcatattgaa ttgctccgaa tgtg                                    24

<210> SEQ ID NO 11
<211> LENGTH: 17
<212> TYPE: DNA
<213> ORGANISM: Artificial Sequence
<220> FEATURE:
<223> OTHER INFORMATION: Synthetic probe

<400> SEQUENCE: 11
ggcgtatgca caacgca                                            17

<210> SEQ ID NO 12
<211> LENGTH: 21
<212> TYPE: DNA
<213> ORGANISM: Artificial Sequence
<220> FEATURE:
<223> OTHER INFORMATION: Synthetic probe

<400> SEQUENCE: 12
gcgacagctg accagtcagc a                                       21

<210> SEQ ID NO 13
<211> LENGTH: 18
<212> TYPE: DNA
<213> ORGANISM: Artificial Sequence
<220> FEATURE:
<223> OTHER INFORMATION: Synthetic probe

<400> SEQUENCE: 13
cactcctcca cagctcct                                           18

<210> SEQ ID NO 14
<211> LENGTH: 15
<212> TYPE: DNA
<213> ORGANISM: Artificial Sequence
<220> FEATURE:
<223> OTHER INFORMATION: Synthetic probe
```

```
<400> SEQUENCE: 14
acatgtactc actgg                                                          15

<210> SEQ ID NO 15
<211> LENGTH: 18
<212> TYPE: DNA
<213> ORGANISM: Artificial Sequence
<220> FEATURE:
<223> OTHER INFORMATION: Synthetic probe

<400> SEQUENCE: 15
ctcacatgtg gtcctctg                                                       18

<210> SEQ ID NO 16
<211> LENGTH: 22
<212> TYPE: DNA
<213> ORGANISM: Artificial Sequence
<220> FEATURE:
<223> OTHER INFORMATION: Synthetic probe

<400> SEQUENCE: 16
gtcctgttga cctatccact gc                                                  22
```

ANALYSIS OF ALPHA INTEGRINS FOR THE DIAGNOSIS OF DIABETIC NEPHROPATHY

This application is a Nonprovisional of U.S. Provisional Application No. 60/001,387 filed on Jul. 21, 1995; U.S. Provisional Application No. 60/001,861 filed on Aug. 3, 1995; and U.S. Provisional Application No. 60/016,700 filed May 2, 1996.

BACKGROUND OF THE INVENTION

Diabetic nephropathy is a major cause of renal failure in the U.S. and develops in approximately 30% of insulin dependent diabetes mellitus (IDDM) patients. Recent studies by the Diabetes Control and Complications Trial Group have indicated that intensive insulin treatment substantially reduces the risk of developing complications, including nephropathy. However, the cost and effort of the intensive therapy, as well as the danger of hypoglycemic attacks dictate that this treatment should be limited to those patients who are prone to develop complications. It follows that an early selection of these diabetic subjects would be extremely helpful, but currently there are no adequate predictors available for clinical use.

Metabolic imbalance caused by hyperglycemia has been implicated as a major factor in the development of this condition and is associated with a genetic tendency to develop nephropathy. A prominent expansion of the mesangium with changes in the composition of the mesangial matrix have been observed in diabetic nephropathy (Williamson et al., *Diabetes Met. Rev.* 4:339 (1988), Steffes, M. W., et al. *Diabetes* 38:1077–81 (1989)).

Studies performed with human and experimental animal mesangial cells cultured in high-glucose medium have demonstrated an increased synthesis and accumulation of matrix proteins, namely collagens, including collagen type IV and fibronectin. This suggests that hyperglycemia plays a role in the mesangial changes of diabetic nephropathy. Ayo, S. H., et al. (1990a), *Am. J. Pathol.* 136:1339–1348; Nahman, N. S., et al., *Kidney Int.* 41:396–402 (1992); Danne, T., et al., *Diabetes* 42:170–177 (1993). The changes in the matrix secretion pattern of the cell are mediated either directly by hyperglycemia or by the glycation of mesangial matrix on prolonged exposure to high levels of glucose. Studies have demonstrated that cultured mesangial cells are influenced by the glycation of matrix leading to altered cell adhesion, spreading and proliferation. Since collagen IV (cIV) is the major component of the mesangial matrix (about 60%), changes in the interactions between this major mesangial glycoprotein and mesangial cells may play an important role in the pathology of diabetic nephropathy. Kim, Y., et al., *Am. J. Pathol.* 138:413–420 (1991). The changes in matrix deposition are secondary in time to insulin insufficiency. Altered matrix deposition including basement membrane thickening is also found in a variety of arterioles and arteries in patients with diabetes mellitus. Altered matrix deposition is found in the pancreas of diabetic patients. Altered matrix deposition puts diabetic patients at risk for developing secondary pathological changes including, but not limited to nephropathy, myocardial infarction, cerebral stroke, problems associated with reduced circulation, retinopathy, neuropathies and the like.

Cell-matrix interactions are mediated, for the most par; by a family of receptors known as integrins. The very late antigen (VLA) subgroup of integrins which share a common β1 chain, include the cell membrane receptors for cIV, α1β1 and α2β1. Although integrins are mainly studied for their role in cell differentiation, migration and signaling events, they may also be involved in the maintenance of tissue structure. For instance, cells can modify their matrix by altering the production of matrix proteins and/or by regulating matrix organization. Cells cultured under high glucose conditions resulted in an increased production of matrix components by mesangial cells. (Kashgarian, M., et al., *Kidney Int.* 41:524–529 (1992).) The balance of cell surface integrin expression has been demonstrated to be altered in various disease states including inflammation and malignancy (Waes and Carey, *Otolarnyngologic Clinics of North America* 25(5):1117 (1992); Adams, J. C., et al., *Cell* 63:425–435 (1990); Rozzo et al., *FEBS Letters* 332:263 (1993)). This altered expression has been associated with altered adhesion to extracellular components.

Presently, the only earliest available indicator of kidney changes is microalbuminuria which occurs after the appearance of nephropathic changes. Yet only a percentage of individuals with microalbuminuria go on to develop glomerulopathy. Individuals at risk for developing glomerulopathy are best treated with intense glucose-modulating therapies that have their own risk. Often physicians are hesitant to place individuals with microalbuminuria on such therapies since the majority of these patients do not proceed to glomerulopathy. Biopsies indicating the accumulation of matrix accompanying the expansion of the mesangium occur at a point when the process has become irreversible. Therefore an early predictor of nephropathy or other disease states associated with altered matrix deposition would be beneficial as an indicator of those patients who require stringent control of blood glucose levels to minimize nephropathic and other altered matrix deposition-associated disorders.

Thus, there is a need to identify markers associated with the changes seen in nephropathy and in other altered matrix deposition-associated disorders for the diagnosis of these disorders. There is a need to identify changes in regulation and function of integrins in diabetic patients and there is a need to develop a diagnostic test that can be used to identify patients who are likely to develop or have the early symptoms of nephropathy.

SUMMARY OF THE INVENTION

Alterations in the amounts and patterns of alpha-integrin subunits has now been correlated to the onset of nephropathy. Analysis of alpha integrin subunit expression as compared with controls provides a diagnostic tool for the determination of patients likely to develop severe nephropathy and a method to monitor progress of disease during treatment protocols.

Cells that express alpha integrins, such as kidney tissue, fibroblasts, endothelial cells, and blood cells are analyzed for alpha integrin subunit expression, for example, by in situ hybridization methods. Changes in the amounts and pattern of integrin subunit expression as compared with control samples, is diagnostic of nephropathy and can be used to screen individuals, e.g., diabetic patients at risk for developing severe disease.

Analysis of α1, α2, α3, α5, and beta-1 integrin subunit expression as compared with control tissue expression is preferred. An increase in α2, α3, α5, or beta-1 integrin expression and/or a decrease in α1 expression is diagnostic of increased risk of nephropathy. An especially preferred diagnostic method is the comparison of α1 and α2 integrin subunit expression with control tissue. A pattern change including a decrease in α1 and an increase in α2 is diagnostic of increased risk of nephropathy or onset of the disease.

DETAILED DESCRIPTION OF THE INVENTION

Figure 1:
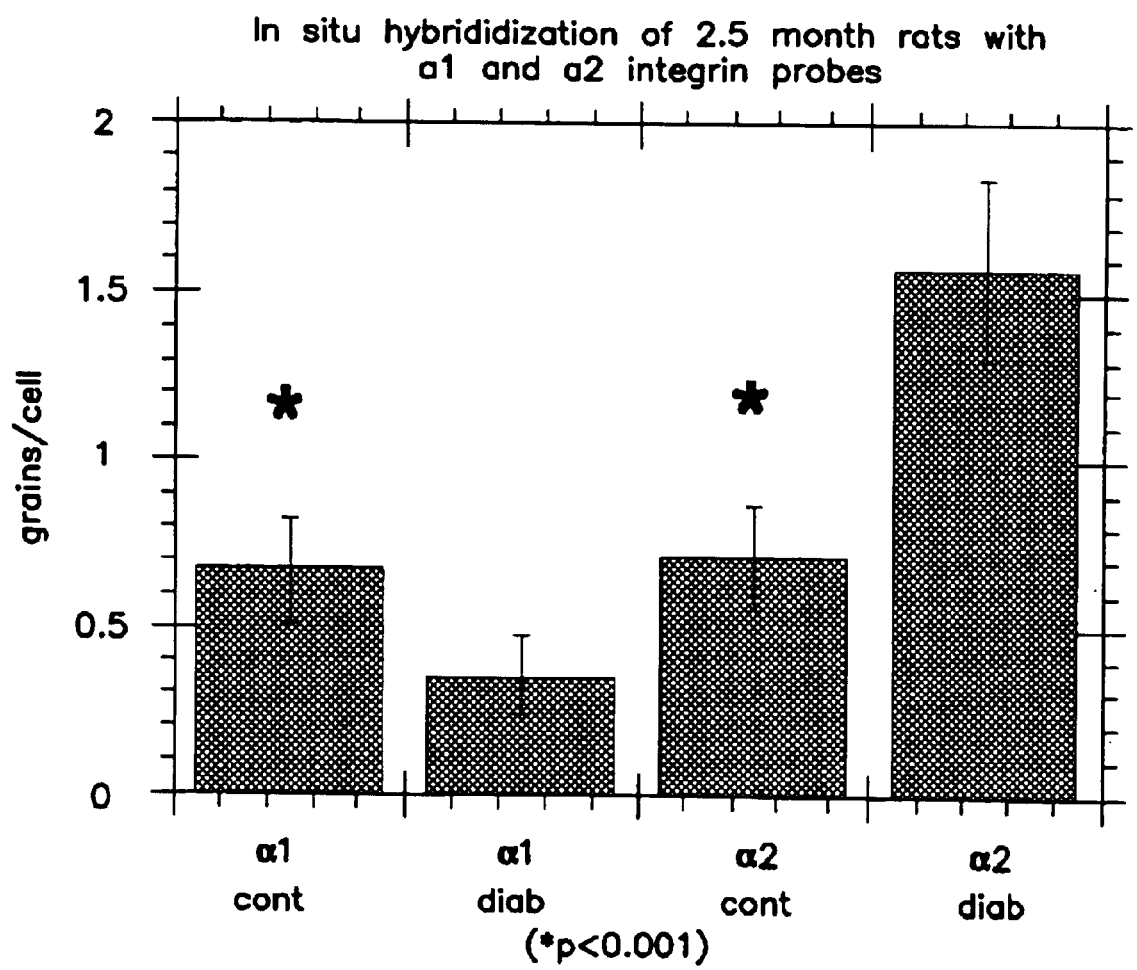
FIG. 1 is a histogram summarizing results of In situ hybridization studies of rat control and diabetic tissue with α1 and α2 integrin probes.

Analysis of changes in the pattern of integrin subunit expression, particularly of alpha integrin subunits, is made by comparing expression in sample tissues as compared with tissue controls.

Tissue Samples:

The invention is directed to methods of detecting changes in a integrin subunit expression in cells, such as the cell populations (visceral epithelial, endothelial and mesangial and other matrix-producing cells) present in the glomerulus; and also in the tubules as well as including, but not limited to, fibroblasts (for example see D. Kyu Jin, et al. in *J. Am. Society of Nephrology*, 5(3): 966, 1994), epithelial, and endothelial cells from a variety of tissues and organs as well as blood cells including, but not limited to polymorphonuclear leukocytes, monocytes, and the like. Changes to blood cells, including leukocytes, have been reported in diabetic patients who develop nephropathy (Ng, et al. *Diabetologia* 33:278–284, 1990).

A change in the expression of α1 and α2 integrins has been detected in the studies disclosed here, under conditions of high glucose (i.e., about 25 mM) compared with low glucose (i.e., about 5 mM), in diabetic test animals in vitro, and in a human diabetic patient with neuropathy. Mesangial cells cultured in high glucose showed an increase in α2 integrin expression and a decrease in α1 integrin expression compared with mesangial cells grown under low glucose conditions. A change in expression of α integrins such as α1 and/or α2 subunits can be used to identify patients that have or will develop diabetic nephropathy. In view of these studies, it is believed that patients showing about a 25 to 100% decrease in α1 integrin and/or about a 25 to 100% increase in α2 integrin expression have a greater chance of developing diabetic nephropathy. The methods disclosed here are useful to identify diabetic patients at risk for developing diabetic nephropathy. The methods may also be useful to monitor progression of diabetic nephropathy. Patients identified as having a risk for developing or showing early symptoms of diabetic nephropathy can be placed on a strict glucose control regimen so that the development and/or progression of nephropathy can be inhibited.

Changes in integrin subunit expression in diabetic patients have been identified in cultured human skin fibroblasts taken from skin biopsies (D. Kyu Jin, et al., *J. Am. Soc. of Nephrology* 5(3):966, 1994) suggesting that a variety of integrin-expressing cells could be monitored to identify individuals with a predisposition to nephropathy or to other complications associated with diabetes-induced altered matrix deposition.

Method of Detecting a Change in Expression of α1 and/or α2 Integrin Subunits in Cells from Diabetic Patients The methods of the invention are conducted with cell types that express alpha (α) integrin subunits. Preferably, to identify patients predisposed to nephropathy, the cells are obtained from tissue samples from biopsy of kidney tissue of diabetic patients. However, other cell types that express a integrin subunits can be utilized including, but not limited to, fibroblasts, endothelial cells, polymorphonuclear leukocytes, monocytes, and other blood cells. The amount of cells typically obtained is relatively small so that the detection methods selected are those that can detect and/or quantitate α integrin subunit expression in a small cell sample. These methods include, but are not limited to in situ hybridization, including polymerase chain reaction (PCR) enhanced in situ hybridization (also known as in situ PCR) and the like.

The cell samples are obtained from patients having diabetes but having no demonstrable symptoms or signs of nephropathy. The earliest change in nephropathy is the detection of microalbuminuria. Biopsy specimens may also be obtained from diabetic patients that may have early symptoms of nephropathy so that the progression of diabetic nephropathy can be monitored. Blood samples and skin biopsies also can be obtained from patients with diabetes and processed for either in situ hybridization or PCR enhanced in situ hybridization (also known as in situ PCR). Similarly, it is possible to perform in situ hybridization or PCR enhanced in situ hybridization using a cheek scraping or a scraping of other accessible tissue.

Biopsy tissue samples are usually about 1 mm$^3$ and are obtained using standard biopsy methods. Where the kidney is the organ selected for biopsy, kidney tissue from the cortical region is preferred although biopsy samples can be obtained elsewhere. Fibroblasts can be obtained from skin or any other tissue. The biopsy samples are then frozen in liquid nitrogen or fixed in 4% fresh paraformaldehyde and sectioned into 5 μm thick sections on silane-coated slides. The sections can then be treated with reagents to detect and/or quantitate α integrin expression in cells.

Blood cells and other α integrin expressing cells can also be analyzed for changes in α integrin subunit expression. These cells include fibroblasts, monocytes, polymorphonuclear leukocytes and other blood cells. Cells can be obtained and isolated from a blood or bone marrow sample. Methods for isolating particular cell types from a blood sample are well known in the art. Preferably leukocytes are isolated from blood by centrifugation, followed by hypotonic shock of residual blood cells as disclosed by Ng, et al. *Diabetologia* 33:278–284, 1990.

Rather than preparing cell sections, the sample of cells can be extracted to obtain nucleic acids using standard methods. The nucleic acids encoding α1 and/or α2 integrin subunits can be amplified using any of a variety of polymerase chain reaction methods. For example, changes in the level of expression of α1 and/or α2 integrins can be detected using a competitive PCR method as described by Gilland, G., *Proc. Natl. Acad. Sci.* (*USA*) 87:2725 (1990).

In a method of the invention, the level of α1 integrin expression is detected and/or quantitated in cells such as glomerular and tubular kidney cells. The level of all integrin expression can be detected using a variety of standard methods. The preferred methods are in situ hybridization, in situ PCR for detection of integrin RNA and immunofluorescence detection of antibody-tagged integrin protein. A decrease of about 25 to 100% in α1 integrin expression can indicate that early changes of diabetic nephropathy are occurring and can be used to identify patients that have an increased risk of developing diabetic nephropathy. A decrease in α1 integrin expression is compared to the level of α1 integrin expression in cells from age matched non-diabetic controls.

For detection and quantitation using in situ hybridization, the following method is preferred: a detectably labeled probe that is complementary to and/or hybridizes to all or a portion of nucleic acid sequences encoding all or a portion of α1 integrin subunit is utilized. A radioactively labeled probe preferably has a specific activity of about 2×10$^8$ to $1 \times 10^9$ dpm/µg. In situ hybridization on cells such as kidney tissue can be conducted as follows. 5 µm tissue sections, fibroblasts and/or blood cells on silane-coated slides are further fixed in fresh 4% paraformaldehyde for 10 min. The slides are then pretreated with 0.2N HCl for 20 min., 0.05 M Triethanolamine (TEA, Sigma) for 15 min, 0.005% digitonin for 5 min., 3 µg/ml proteinase K (Sigma) for 15 min. at 37° C., and 0.3% acetic anhydride—0.1M TEA for 10 min. Hybridization is performed at 50° C. overnight in 50% formamide, 0.6 M NaCl, 1×Denhardt's, 0.17 µg/ml human $COT^{RT}$ DNA (GIBCO/BRL), 1 mg/ml poly A (Boehringer Mannheim), 10% (W/V) Dextran sulfate (Sigma), 0.1 M dithiothreitol (DTT, Boehringer Mannheim), 1 mM EDTA, 0.1 mM aurinitricarboxylic acid (ATA, Sigma) and $S^{35}$-dCTP labeled cDNA probe. The following day, the slides are washed in 2×SCC-0.05% SDS for 60 min. at 55° C.; further washed in the high stringency washing buffer containing 50% formamide, 0.6 M NaCl, 1 mM EDTA, 5 mM DTT and 10 mM Hepes for 4 days at room temperature. After 4 days, the slides are rinsed in 2×SCC and the slides are dehydrated in graded ethanol with 0.3 M ammonium acetate, then dipped in Kodak NTB-2 emulsion and exposed for 5 days at 4° C. After development, the slides are stained with hematoxylin-eosin (Surgipath Canada, Inc., Winnipeg, Canada) and mounted. The silver grain number per cell are used to quantitate the result of in situ hybridization. About 10–20 glomeruli and a similar number of tubules are examined per patient.

A probe of the invention hybridizes to and is complementary to and/or all or a portion of a nucleic acid sequence encoding α1 integrin as long as the probe specifically detects α1 integrin expression. Probes can be designed using a known sequence such as the rat α1 integrin sequence as shown as FIG. 2 in Takada and Hemnlev, *J. Cell Biol.* 109:397–407 (1983) or by the use of commercially available programs and are capable of binding to rodent or human α1 integrin but are not capable of binding to other proteins including other proteins having regions homologous to a integrins when tested under identical hybridization conditions. Examples of other proteins that have homologous regions to α integrins include those proteins identified using a gene bank search, such as GenBank, or the like, or in publications related to α1 and α2 subunits (for example, see Ignatius, et al. *J. Cell Biol.* 111:709–720, 1990 listing proteins with homologies to the α1-subunit).

The probe can be about 15 nucleotides long up to a full length probe of about 4 kb. The probes are preferably 100% complementary to the nucleic acid encoding α1 integrin however some mismatches can be present depending on the length of the probe. About 1 to 3 mismatches in a probe of about 20 to 30 nucleotides long can be present as long as hybridization conditions are adjusted to account for mismatches. Hybridization conditions can be adjusted to take into account mismatches in accord with known principles as described in Sambrook et al., *A Guide to Molecular Cloning*, Cold Spring Harbor N.Y. (1989).

A specific example of a nucleic acid sequence encoding α1 integrin is the rat α1 integrin sequence shown as FIG. 2 in Ignatius et al., *J. Cell. Biol.* 111:709–720, 1990, (SEQ ID NO:1) and the protein sequence encoded by α1 integrin is provided as SEQ ID NO:2. A DNA sequence encoding α1 integrin can be obtained from a rat pheochromocytoma cell line PC12 as described by Ignatius et al., *J. Cell. Biol.* 111:709 (1990). Briefly, a cDNA library can be prepared from rat pheochromocytoma PC12 in a lambda vector. The sequence can be identified and/or amplified using probes or primers designed from the known sequences using standard methods as described in Sambrook et al., (supra). Once the sequence is subcloned it can be confirmed by sequence analysis and/or by screening with antibodies specific for α1 integrin. Other DNA sequences encoding α1 integrins can be identified and isolated using probes and primers derived from the known sequences.

A preferred probe is a 3.9 kb fragment from the 5' end through the EcoRI site near base 3900 including the sequence as shown in FIG. 2 of Ignatius et al. (supra). Smaller fragments that can form probes can readily be prepared with restriction enzymes or derived by automated or manual oligonucleotide synthesis techniques, by PCR, or by other methods also known in the art. The probes are preferably detectably labeled with a radioactive nucleotide using standard methods.

Other methods utilizing probes for detection of α1 integrin expression can also be utilized using standard methods such as Northern Blot Analysis and the like as described in Sambrook et al., cited supra.

Primers can also be designed based upon the sequence of rat α1 integrin sequence. This invention also contemplates using primers and nucleic acid sequences from the human α1 integrin sequence provided by Briesewitz, et al. (*J. Biol. Chem.* 268(4):2989–96, 1993). Primers can be designed using a known sequence using commercially available computer programs. Primers typically are complementary to and/or hybridize to a 5' region and/or a 3' region of the nucleic acid sequence encoding the protein of interest. The primers can be used to amplify all or a portion of DNA or cDNA encoding α1 integrin. Primers can be used to make probes and to detect expression levels of α1 integrin. Primers preferably have at least 15 nucleotides that are 100% complementary to the nucleotide sequence selected. The primers can also have additional sequences preferably at the ends of the primer that include restriction enzyme sites and the like that are not complementary to the nucleic acid sequence to be amplified. Primers are preferably about 15 to 50 nucleotides long and can be prepared by automated synthesis.

The primers can be used to detect the level of α1 expression in cells. RNA from cells is extracted and reverse transcribed using standard methods. Primers that are complementary to and can hybridize to a DNA sequence encoding α1 integrins are utilized to amplify the cDNA. A decrease in the level of PCR product can be determined in comparison to the amount of PCR product obtained from control cells.

One method of utilizing PCR to detect α1 integrin expression is in situ PCR. A method for PCR in situ hybridization is described in *PCR In Situ Hybridization Protocols and Applications*, J. Novo ed., "PCR In Situ Hybridization", pp. 157–183. Briefly, tissue sections, fibroblasts and/or blood cells (about 5 µm) are placed on silane-coated glass slides. After removing paraffin, the slides are treated with trypsinogen (2mg/ml) in 0.01N HCl for 10 minutes and then trypsinogen inactivated in 0.1M Tris HCl (pH 7.0) solution. The slides are washed sequentially in 90% and 100% ethanol, two times for 1 minute each and air dried. Aliquots of reaction mixture containing 0.15 units/ml Taq DNA polymerase and specific primer pairs for α1 integrin are added to the tissue section and then overlaid with siliconized glass coverslips. The slides are placed in the heat-sealable plastic bags and 4–5ml mineral oil is added. After removing air, the bag is heat-sealed and placed in the thermal-cycling oven for 40 cycles. After thermal-cycling, the slides are washed twice in chloroform for 2 minutes. The coverslips are removed and the slides are dipped briefly in fresh chloroform. After washing in PBS for 5 minutes, the slides are dehydrated and air-dried. The slides are dipped in NTB2 nuclear emulsion (Kodak) and exposed in the dark for 7 days. After development, the slides are counterstained with hematoxylin-eosin.

A change in the level of α1 integrin protein expression can also be detected by using immunofluorescence. (Unless otherwise specified as "protein expression", the term "expression" used herein generally refers to RNA expression.) Sections of tissue samples, fibroblasts and/or blood cells can be stained with antibodies specific for α1 integrin. It is preferable that antibodies are monoclonal antibodies and are antibodies that do not substantially cross-react with other α integrin subunits. Antibodies to α1 integrin can be made by standard methods such as described in Wayner E A and W G Carter, 1987, *J. Cell Biol.* 121(5): 1141–1152. Antibodies specific to α1 integrin include the SR84 and TS2/7 antibodies. Information related to these antibodies is provided in Examples 1 and 3. A decrease in the level of immunofluorescence can be observed and quantitated using standard methods. A decrease of about 25 to 100% of α1 integrin expression may be used to identify patients that have a greater risk of developing diabetic nephropathy. A decrease in α1 integrin expression is compared to the level of α1 integrin expression in age-matched nondiabetic controls.

The preferred method of the invention involves comparing the level of expression of α2 integrin to the level of expression of α1 integrin. Under high glucose conditions, a decrease in the level of α1 expression is seen as well as an increase in the level of α2 expression in mesangial cells. It is believed that patients at greater risk for nephropathy or other complications associated with diabetes will exhibit an increase in α2 expression and a decrease in α1 expression. A change of about 15 to 100%, and preferably of about 25 to 100%, of α2 integrin expression as well as a change of about 15 to 100%, and preferably of about 25 to 100%, of α1 integrin expression is believed to be indicative of patients with a greater risk of developing diabetic nephropathy.

Integrin expression is associated with a variety of cell types in a variety of locations throughout the body, therefore it is possible that altered levels of integrin expression will also be identified in diabetic associated retinopathy, atherosclerosis and select diabetic neuropathies.

The expression of integrin subunits, preferably of α1 and α2 integrin subunits, is detected and/or quantitated in tissue samples, fibroblasts and/or blood cells from diabetic patients. The preferred methods are those that allow detection of gene expression in a small amount of cells or tissue.

The expression of α2 integrin can be detected using in situ hybridization. The conditions for in situ hybridization are the same as those described previously. A probe specific for nucleic acid sequences encoding α2 integrin can be prepared using standard methods as described in Sambrook et al., cited supra. The probes are complementary to and/or hybridize to all or a portion of a nucleic acid sequence encoding α2 integrin. As described for α1 integrin, the probe to detect α2 integrin can hybridize to a portion of a nucleic acid sequence as long as the probe specifically detects a sequence encoding α2 integrin. Nucleic acid sequences can be DNA, cDNA, or RNA. It is preferred that the probe hybridize to RNA or cDNA.

A specific example of nucleic acid sequence encoding α2 integrin is shown in FIG. 2 of Takada and Hemler, *J. Cell Biol.* 109:397 (1989). (SEQ ID NO:3). DNA sequence encoding human α2 integrin can be isolated as described in this reference. The protein encoded by SEQ ID NO:3 is provided in this disclosure as SEQ ID NO:4. Nucleic acid sequences encoding α2 integrin can be obtained from human lung fibroblasts and/or human endothelial cells. Preferably DNA libraries from endothelial cells can be prepared and nucleic acids encoding α2 integrin identified and/or amplified using probes and primers derived from the sequence of α2 integrin, e.g., as shown in FIG. 2 of Takada et al. (supra). If primers are selected, DNA sequences can be amplified using the polymerase chain reaction and then subcloned. Clones that are positive by hybridization to a probe specific for DNA sequences encoding α2 integrin (see Examples 1 and 3) or that express proteins that are positive by reacting with an antibody specific to α2 integrin such as P1H5 are selected. A DNA sequence encoding α2 integrin can be confirmed by DNA sequencing in comparison to the known α2 sequence, as shown in FIG. 2 of Takada et al. (supra).

A probe of the invention hybridizes to and is complementary to and/or hybridizes to all or a portion of a nucleic acid sequence encoding α2 integrin as long as the probe specifically detects α2 integrin expression. Probes can be designed using a known sequence such as shown in FIG. 2 of Takada et al. (supra) by the use of commercially available programs.

The probe can be about 15 nucleotides long up to a full length probe of about 5 Kb. The probes are preferably 100% complementary to the nucleic acid encoding α2 integrin however some mismatches can be present depending on the length of the probe.

About 1 to 3 mismatches in a probe of about 20 to 30 nucleotides long can be present as long as hybridization conditions are adjusted to account for mismatches. Hybridization conditions can be adjusted to take into account mismatches in accord with known principles are described in Sambrook et al., *A Guide to Molecular Cloning*, Cold Spring Harbor N.Y. (1989).

A preferred probe is 1.8 fragment kb from the 5' end through the EcoRI site near base 1800 of the sequence shown in FIG. 2 of Takada et al. (supra). Other probes can be derived from this fragment or from the full length sequence by use of restriction enzyme digestion. Probes can also be prepared by automated synthesis or by PCR. Probes are preferably delectably labeled with a radioactive nucleotide using standard methods.

Probes specific for α2 integrin expression can then be utilized in methods of detecting α2 integrin expression in various cell types. The preferred method is by use of in situ hybridization or PCR-in situ hybridization on kidney as well as other tissues. The method utilized for in situ hybridization has been described previously (Takada and Hemler, supra). The method for PCR in situ hybridization has been described for α1 integrin. Other methods utilizing probes for detection of α2 integrin expression can also be utilized using standard methods such as Northern Blot Analysis, and the like, as described in Sambrook et al. cited supra.

Primers can also be designed based upon the known DNA sequence encoding human α2 integrin. Primers can be designed from a known sequence such as shown in FIG. 2 of Takada et al. (supra), using commercially available software. Primers typically are complementary to and/or hybridize to a 5' region and/or a 3' region. The primers can be used to amplify all or a portion of DNA or cDNA encoding α2 integrin. Primers can be used to make probes and to detect expression levels of α2 integrin. Primers preferably have at least 15 nucleotides that are 100% complementary to the nucleotide sequence selected. The primers can also have additional sequence preferably at the ends of the primer that include restriction enzyme recognition sites and the like. Primers are preferably about 15 to 50 nucleotides long and can be prepared by automated synthesis.

Primers can be used to detect the level of α2 integrin expression in cells. Nucleic acids, preferably RNA, from cells from diabetic patients are extracted and reverse tnanscribed using a standard method. Primers that are complementary to and can hybridize to a cDNA sequence encoding α2 integrin are utilized to amplify the cDNA. An increase in the level of PCR product can be determined in comparison to the amount of PCR product obtained from control cells.

A change in the level of α2 integrin protein expression can also be detected by using immunofluorescence. Sections from kidneys and/or other tissues, skin fibroblasts and/or blood cells can be incubated with antibodies specific to α2 integrin. It is preferable that the antibodies are monoclonal antibodies and are antibodies that do not crossreact with other a integrin subunits. Antibodies to α2 integrin can be made by standard methods such as described in Wayner E A and W G Carter, 1987, *J. Cell Biol.* 121(5):1141–1152. Antibodies specific for α2 integrin include P1H5. An increase in the level of immunofluorescence can be observed and quantitated using standard methods such as flow cytometry. An increase of about 25 to 100% of α2 integrin expression can be used to identify patients that have a greater risk of developing diabetic nephropathy. An increase in α2 integrin expression is compared to α2 integrin expression in nondiabetic control cells.

An increase in α2 integrin expression alone can also be used to identify a patient that may have a greater risk of developing diabetic nephropathy. An increase in α2 expression can be determined as described using the methods described above. An increase of about 25 to 100% in α2 integrin expression may indicate a patient who has an increased risk of developing diabetic nephropathy.

Although an increase of α2 integrin expression or a decrease of α1 integrin expression alone can be utilized to identify patients at greater risk for developing diabetic nephropathy, a preferred method is to detect changes in both α1 and α2 integrin expression. It is believed that an increase in α2 integrin expression and a decrease in al integrin expression identifies patients that are at greater risk of or are showing early symptoms of diabetic nephropathy.

In one step of the method, the level of α2 to α1 integrin is compared. The level of α1 integrin expression can be detected and/or quantitated using the methods described previously. The level of α1 and α2 integrin expression can be quantitated on two different cell samples such as two sections of the same tissue sample. About 10–20 glomeruli and tubules are examined. On one cell sample containing the same type of cells, α2 integrin expression can be quantitated and on a second cell sample with the same type of cells, α1 integrin expression can be quantitated. Alternatively, the level of α1 and/or α2 integrin expression can be determined using the same cell sample if the agent used to detect α1 expression is detectably labeled with a first detectable label and the agent used to detect α2 expression is detectably labeled with a second detectable label. The first detectably labeled agent and the second detectably labeled agent are agents selected that can be detected and/or quantitated in the presence of one another.

In a preferred version, kidney tissue sections taken from diabetic patients are fixed in formalin and then treated with HCl and proteinase K. A first probe specific for α1 integrin is α3.9 kb fragment from 5' end through EcoRI site near base 3900 probe including a sequence as shown in FIG. 2 of Ignatius et al. (supra). This probe is labeled with $^{32}$p or 35S or other suitable labels known in the art including, but not limited to, fluorescent labels, biotinylated labels, or other radio labels and the like. The probe is incubated with the section as described previously. A second section taken from the same tissue sample is treated in the same manner but incubated with a probe specific for α2 integrin expression. In a preferred embodiment, a probe specific for α2 integrin expression is α1.8 kb fragment from 5' end through EcoRI site near base 1800 that includes a sequence as shown in FIG. 2 of Takada et al. (supra). Both probes are labeled with $^{32}$p or $^{35}$S. The probe is incubated with the section overnight at 50° C. and then for 4 days at room temperature. The sections are then developed for autoradiography. The number of grains per cell are counted for about 10–20 glomeruli and tubules. The total counts for α2 integrin expression vs. α1 integrin expression are compared. An increase of about 40% in α2 integrin and α30–40% decrease of α1 integrin may indicate a patient is at greater risk for developing diabetic nephropathy.

In an alternative version, the level of expression of α2 integrin is compared with the α1 expression which can be determined using in situ PCR or competitive reverse transcriptase PCR. Primers specific for α1 and α2 integrin expression can be prepared as described previously. For competitive reverse transcriptase PCR, RNA extracted from different cell types obtained from diabetic patients will be reverse transcribed to generate cDNA. The cDNA will be mixed with the various concentrations of competitive template amplified by the PCR method. After degradation of competitive cDNA with restriction enzyme, amplified cDNA will be subjected to electrophoresis in 2% agarose gel, electrotransferred to a nylon membrane, UV cross-linked to the membrane and hybridized with a $^{32}$P-labeled probe. Autoradiographs will be used to quantify the label bound to the cDNA using amount of label bound to samples containing target cDNA alone as compared to samples also containing competitor cDNA to arrive at the target cDNA concentration. For in situ PCR, a method has been described previously. The change in α1 and α2 integrin expression can be quantitated by counting the number of grains per cell in control vs. diabetic cells.

Optionally, for each of the detection methods for α integrin subunits, the level of integrin subunit expression can be compared to expression of a control. The control is selected to be a protein expressed at the same levels in both normal and diabetic cells. The control protein is also selected to be one that is expressed at sufficient levels for easy detection and quantitation. The level of expression of α1 and α2 integrin expression can each be compared to that of the level of the control RNA expression in the cells. The level of RNA expression of α1 integrin or α2 integrin can be divided by the level of expression of the control RNA to normalize the values to the level of control expression in a particular cell sample. The level of expression of the control protein is detected and quantitated using the same method as α1 or α2 integrin expression. The preferred control protein is a cell surface HLA determinant.

Optionally, the levels of α3, α5, or beta-1 integrin subunit expression can be analyzed as described above. The level of α3, α5, or beta-1 integrin expression in cells such as kidney tissue can be detected and quantitated as described for α1 and α2 integrin expression including in situ hybridization, in situ PCR, immunofluorescence and the like. Other cell types can be analyzed as described above, including fibroblasts and blood cells. Antibodies specific for α3, α5, and beta-1 can be prepared as described by Wayner et al. cited supra.

A DNA sequence encoding α3 integrin has been described in Takada et al., *J. Cell Biol.* 115:257 (1991). A probe specific for cDNA sequence encoding α3 integrin subunit is 1.4 Kb SalI fragment containing 5' untranslated and amino terminal coding sequences for α3 subunit of integrin. DNA sequences encoding α3, α5, and beta-1 integrin can be utilized to form primers and probes as described previously.

The level of α3, α5, or beta-1 integrin expression is increased about 15 to 100% compared with cells from age matched nondiabetic controls. It is believed that an increase in α3, α5, or beta-1 integrin subunit expression may also identify patients that have an increased risk of developing diabetic nephropathy or that have early signs of diabetic nephropathy.

This invention also relates to methods for detecting alterations in integrin subunit expression, particularly α1 and/or α2 integrin subunit expression by obtaining a cell sample from a patient, processing the sample to detect alterations in integrin subunit expression as compared to integrin expression in samples from age matched normal controls, detecting levels of integrin expression and determining if these levels are altered relative to controls.

This method is useful for predicting individuals at risk for developing pathologies associated with altered cell matrix deposition, including but not limited to renal nephropathy. In preferred embodiments of this invention, the tissues used to detect altered α1 and/or α2 integrin expression include kidney biopsies, skin biopsies and blood cells including polymorphonuclear cells, monocytes, and other cells expression integrin subunits. Biopsied tissue can be further separated into its cellular components or processed as tissue sections for in situ hybridization techniques, and/or for immunodiagnostic techniques including immunofluorescence and immunoperoxidase staining.

The cellular components of the biopsied tissue can be cultured for in vitro studies including Northern procedures, PCR techniques, immunofluorescent techniques and/or in situ hybridization techniques. Alternatively, cells can be separated and analyzed by flow cytometry, immunofluorescence, processed for PCR or for any of a variety of techniques discussed throughout this disclosure.

While blood cell components are preferably separated from the whole blood sample using methods well known in the art. Individual cells are separated, where necessary, using techniques such as those of Ng, et al. (supra), and Baron, et al. *Clin. Sci.* 37:205–219, 1990. Preferably the samples are tested using in situ hybridization methods. Where the amount of tissue available is fairly small, PCR-enhanced in situ hybridization can be used.

The present invention is also directed to a kit to detect alterations in integrin subunit expression, particularly α1 integrin and/or α2 integrin subunit expression in a patient sample. A variety of kits are contemplated to encompass a variety of methods. These kits optionally include reagents to process a tissue or cell sample for the technique employed by that particular kit. By example, a kit for PCR or PCR enhanced in situ hybridization can include reagents to process the cell sample or section and isolate the RNA (for PCR). It will also contain suitable primers to amplify the target sequence and additional probes, if necessary, to detect the desired nucleic acid fragments as well as buffers and reagents for the polymerase chain reaction and the buffers and emulsions required to develop the silver granules, and the like, for in situ hybridization methods. Other kits can alternatively include reagents for immunofluorescence using antibodies to the integrin subunits and/or probes, primers and reagents for modifications of in situ or PCR in situ hybridization methods.

All publications and patent applications in this specification are indicative of the level of ordinary skill in the art to which this invention pertains. All publications and patent applications are herein incorporated by reference to the same extent as if each individual publication or patent application was specifically and individually indicated by reference.

It will be apparent to one of ordinary skill in the art that many changes and modifications can be made in the invention without departing from the spirit or scope of the appended claims.

EXAMPLE 1

Effect of High Glucose on the Synthesis and Cell Surface Expression of Integrin Receptors by Cultured Mesangial Cells Cell Lines and Culture Conditions Human mesangial cells (HMC) were isolated from 19–22 week old fetal kidney tissue or adult tissue as previously described (Striker and Striker, *J. Lab. Invest.* 53(2):122–131, 1985). Cells were cultured at 37° C. in an environment of 95% air and 5% $CO_2$ and in media composed of MEM (Sigma, St. Louis, Mo.) containing 5 or 25 mM glucose, 20% FBS, 15 mM Hepes, penicillin (100 U/ml), streptomycin (100 mg/ml), and amphotericin (25 mg/ml). Cells were cultured in the two different conditions for at least two passages before they were used for experiments. Cells were released from their tissue culture flasks for passaging or for use in experiments, by washing twice with 1 mM EDTA in HBSS and then treating with 0.05% trypsin and 1 mM EDTA in HBSS for 1 min. Cells between passage 4 and 9 were used in experiments.

The cells were grown in T-75 flasks until 75–80% confluent. For the adhesion and immunoprecipitation analyses, cells were metabolically labeled for 18 hours with 0.5 mCi of [$^{35}$S]-methionine per T-75 flask. [$^{35}$S]-methionine was obtained from Du Pont/NEN, Boston, Mass.

Monoclonal Antibodies (Mabs) to Integrin Receptors

Mabs to the integrin receptors α3 (P3D11), α5 (P3D10) and β1 (P5D2) can be produced as previously described (Wayner et al., *J. Cell. Biol* 121(5):1 141 (1993)) and are available from E A Wayner, Fred Hutchinson Cancer Center, Seattle, Wash. The antibodies were characterized by sequential immunoprecipitation with known Mabs directed against these integrin receptors (P1B5, P1D6, P4C10) available from E A Wayner. Other Mabs α2 (P1H5), α4 (P4G9) and β2 (P4H9) were previously described (Wayner et al., cited supra 1993) and are available from E A Wayner, Fred Hutchinson Cancer Center, Seattle, Wash. TS2/7 was provided by Dr. Martin Hemler (Dana Farber Cancer Institute, Boston, Mass.).

SR84 supernatant was used as a function-blocking antiα1 Mab in inhibition experiments. SR84 is available from Dr. D. O. Clegg (Univ. of California, Santa Barbara, Calif.). (α6) G0H3 was purchased from AMAC Inc., Westbrook, Me. In addition monoclonal antibodies to α1 and α2 integrin were obtained from Telios Pharmaceuticals (San Diego, Calif.). Hybridoma culture supernatant or ascites fluid were used for immunoprecipitation, flow cytometry and inhibition experiments. A Mab directed to a cell surface HLA determinant was used as a negative control (W6/32, HB95: American Type Culture Collection, Rockville, Md., USA). W6/32 bound to the surface of cultured mesangial cells but did not influence adhesion of cIV. SP2 myeloma culture supernatant was also used as a control.

Immunoprecipitation Analysis of Integrins from Mesangial Cell Membranes

Mesangial cells metabolically labeled with [$^{35}$S]-methionine were detached from flasks by treatment with trypsin (Sigma) for 2 minutes, washed three times with phosphate-buffered saline (pH 7.4) and resuspended in PBS containing protease inhibitors (1 mM PMSF and 1 mM NEM). The radiolabeled cell membrane proteins were solubilized by adding lysis buffer (1% Triton X-100, 1 mM Calcium, 1 mM PMSF, 1 mM NEM and PBS at pH 7.4) and incubating for 60 minutes at 4° C. Insoluble material was separated by centrifugation at 10,000 rpm for 30 minutes.

The supernatant was transferred and 10 μl was tested for radioactivity ($\geq 10^7$ cpm/per antibody being assayed was considered to be adequate for immunoprecipitation). The lysate was precleared once with fetuin-agarose which was removed by centrifugation at 10,000 rpm for 15 minutes. This was followed by three preclears with protein A agarose bound to rabbit anti-mouse IgG, the last preclear was done overnight.

For immunoprecipitation, the cell lysate (equal counts of lysate for cells in 5 and 25 mM glucose were used) was incubated with the monoclonal antibodies to be tested, pre-bound to rabbit anti-mouse protein A-agarose. Myeloma culture supernatant was used as a negative control. Anti-HLA antibody (W6/32) was used as a control for loading. After an overnight incubation at 4° C., the agarose beads were washed five times and bound material was eluted by boiling for 5 minutes in SDS.

The eluted material was analyzed by loading lysate from each permutation on a 7.5% non-reducing SDS-PAGE gel and labeled proteins were visualized by autoradiography. The fluorograms were scanned with a Macintosh Quadra 840 computer using the NIH Image 5.1 Program, and the optical density of the bands was red after subtracting the background. The O. D. was corrected using the lanes immunoprecipitated with W6/32. Immunoprecipitation assays were performed three times for each growth condition of mesangial cells.

Immunoprecipitates were obtained with anti-integrin monoclonal antibodies from detergent extracts of metabolically labeled human kidney mesangial cells grown in 5 (low) or 25 mM (high) glucose. Equal counts of membrane proteins were immunoprecipitated to compare the level of integrin receptors of mesangial cells under the two growth conditions of low or high glucose levels.

Cells grown in 25 mM glucose have a higher specific activity of labeling than cells in 5 mM glucose. To overcome this difference and permit a comparison of the band intensity on immunoprecipitation equal counts of cell lysate from the two populations were immunoprecipitated with the antibody. Densitometry and statistical analysis of three experiments was performed, the data normalized to the HLA control and expressed as an O. D. ratio of cells grown in high glucose (HG) to cells grown in low glucose (LG), for three experiments, with (LG=1). Cells were labeled with [$^{35}$]-methionine, the cells were harvested, and solubilized. Samples were incubated with antibody and equal counts of cell lysate from the two cell populations were immunoprecipitated with equal amounts of antibody.

The control indicated that there were comparable amounts of cell surface HLA determinant precipitated from each sample. W6/32, a Mab to cell surface HLA determinant was used as a negative control. Other antibodies used included an anti-α1 antibody (TS2/7) and an anti-α2 antibody (P1H5). In total 5 mM and 25 mM glucose exposed cell extracts were immunoprecipitated side by side 3 times.

The α1 subunit band was clearly discernible at 180 kD in cell samples exposed to 5 mM of glucose and was associated with β1 band (116 kD). No α1 band could be seen in the 25 mM treated cell sample. In contrast, the α2 subunit band was more prominent in cell samples exposed to 25 mM glucose and appeared as a band at 130 kD. The 130 kD α2 band was present in 5 mM glucose but was significantly less intense than the 25 mM glucose treated samples.

The cell lysates were also incubated with the following antibodies including: SP2 myeloma culture supernatant; anti-β1 (P5D2), anti-β2 (P4H9), anti-β2 (P1H5), anti-α3 (P3D11), anti-α4 (P4G9), anti-α5 (P3D10) and anti-α6 (G0H3). Result were interpreted from three independent experiments. Immunoprecipitation of α3–α6 and β1 integrin subunits was performed on cells from the two growth conditions. Subunits α4 and α6 were not detected in either cell population. The antibody to the β1 subunit precipitated 116 kD protein, the β1 subunit, and also a precursor β1 band at 105 kD. The α3 and α5 subunits were seen at ≈130 kD with the associated β subunit at 116 kD, in both cell populations.

Flow Cytometry

Cell surface expression of integrin subunits by cultured human mesangial cells was evaluated by indirect immunofluorescence staining and flow cytometry. Mesangial cells were released with trypsin, washed and resuspended in FACS buffer (HBSS, 2% goat serum, 0.02% sodium azide). An equal number of cells, $2 \times 10^5$ were added to each vial.

The cells were incubated with primary antibody for one hour at 4° C. and washed once with 1 ml FACS buffer. The secondary antibody was then added in a total volume of 0.5 ml FACS buffer and incubated for 30 minutes at 4° C. The cells were again washed in 1 ml of FACS buffer and resuspended in 0.5 ml of 2% formaldehyde.

The data was analyzed using CONSORT 30 software on a FACScan (Becton Dickinson, Mountain View, Calif.). Positive fluorescence was determined on a four decade log scale and fluorescence (log F1) was expressed as the mean channel number of 5,000 cells. Cell surface expression experiments were performed in duplicate with each antibody, at least three times with each growth condition of mesangial cells.

Densitometric scanning of the fluorograms generated from metabolically labeled =n cells indicated that the synthesis of the β1 (12%), α3 (14%) and α5 (19%) were moderately increased upon growth in 25 mM glucose. Growth in 25 mM glucose dramatically decreased synthesis of the α1 subunit (39% reduction in intensity) while synthesis of α2 was considerably increased (42%).

These changes in metabolic activity were paralleled by a similar change in the cell surface integrin phenotype of mesangial cells grown in high glucose. To assess the effect of different glucose concentrations in the medium on the levels of mesangial cell surface integrin receptor expression cells in each glucose treatment population were stained for immunofluorescence and processed for flow cytommetry. Mean channel fluorescence (MCN) values of integrin subunit expression were obtained from 3 experiments. Within each experiment the ratio of MCN for cells grown in high glucose (HG) to cells grown in low glucose (LG), denominator=1 was calculated.

Cell surface expression of the following integrin subunits was increased by growth in high glucose: β1 (24%), α2 (26%), α3 (18%), and α5 (19%). The decrease in the synthesis of α1 was reflected in a concomitant decrease in cell surface expression (33% reduction in specific staining). The α4 and α6 subunits were not detectable in cultured mesangial cells either by immunoprecipitation or flow cytometric analyses.

Mesangial cells grown in high glucose (for at least 2 passages) were returned to control media (5 mM glucose), again for at least 2 passages. A flow cytometric analysis of these cells revealed a reversion to "low glucose" type. The expression of α2, α3, α5 and β1 were decreased while the expression of α1 increased (data not shown).

EXAMPLE 2

Adhesion of Cultured Mesangial Cells to Type TV Collagen (cIV): Effect of High Glucose Cell Adhesion to Collagen IV (cIV)

The cells were detached from culture flasks by incubation with trypsin 0.05% and EDTA 0.02% for two minutes at 37° C., then washed twice with DMEM and resuspended to the appropriate concentration in binding buffer (DMEM, 25 mM HEPES, 2 mg/ml BSA at pH 7.4). 48 or 96 well plates were coated overnight at 29° C. with cIV in serial dilutions starting from 100 μg/ml (5 μg/96 well or 20 μg/48 well). Under these conditions approximately 50% of the cIV adhered. To block the remaining reactive sites the plates were treated with 200 μl of BSA at 2 mg/ml for 2 hours at 37° C. 50 μl of suspension containing 5000 cells (96 well plates) or 100,000 cells (48 well plates) was added per well. The plates were incubated at 37° C. in a humidified incubator for approximately 30 minutes. The non-adherent cells were removed by washing three times with binding buffer and then 100 μl of "lysis" buffer (0.5 NaOH, 1% SDS in distilled water) was added to each well for 30 minutes at 60° C. The lysate was transferred to scintillation vials and counted. The data was expressed as a percentage of the total input cpm. Cell adhesion assays were performed in triplicate, at least three times for each growth condition.

Cells grown in medium containing 25 mM glucose adhered significantly better than cells in 5 mM glucose. Adhesion increased with coating concentration of cIV and was saturated at 25 μg/ml for both cell populations.

Inhibition of Cell Adhesion with Monoclonal Antibodies

Since growth in high glucose appeared to alter the synthesis and expression of the integrin receptors α1β1 and α2β1 which have been reported to be involved in cell adhesion to collagen, (Wayner and Carter, *J. Cell. Biol.* 105:1873 (1987)), we examined the effects of glucose on the ability of mesangial cells to adhere to cIV.

Monoclonal antibody inhibition of $^{35}$S-methionine labeled human mesangial cells grown in 5 mM glucose to cIV was assessed. Briefly, 96 or 48 well plates were coated with 50 or 200 μl of cIV at 2.5 μg/ml, overnight at 29° C. The plates were incubated with 2% BSA in PBS to coat remaining reactive sites on plastic for 2 hours, and then hybridoma culture supernatant or ascites containing 10 μg/ml of antibody were added to each well, followed immediately by the cells. After 30 minutes non-adherent cells were washed off and adherent cells were quantitated. Results were obtained from 3 experiments. SP2 myeloma culture supernatant of W6/32 were used as negative controls. A quantitative ELISA was used to determine the concentration of antibody in the hybridoma culture supernatant or ascites.

In each case, the concentration of monoclonal antibody (Mab) was determined relative to a standard curve generated with an isotype-matched control mouse IgG. The concentration of antibody required to saturate the binding sites on human mesangial cells was determined by flow cytometry. The concentration of the antibodies used in the inhibition assays were well above the saturating concentration as determined by flow cytometry. Data were expressed as the percent of maximal binding observed in the presence of W6/32 antibody. Inhibition experiments were performed at least three times, in triplicate, for each growth condition with the various antibodies.

Mesangial cells grown in high glucose (25 mM) adhered better to cIV than cells grown in low glucose (5 mM). Results indicated that adhesion increased with coating concentration of collagen IV and saturated at about 25 μg/ml for both cell populations.

In order to examine the activity of collagen receptors expressed by mesangial cells grown in high glucose, we performed adhesion experiments in the presence of well characterized neutralizing antibodies directed to various β1 integrin subunits. A panel of antibodies was used all of which have been reported to inhibit the adhesion of cells to various substrates (Wayner and Carter, cited supra, 1987; Wayner et al., cited supra, 1993). Antibodies were used at saturating concentrations as determined by immunofluorescence staining and flow cytometry. In the competition experiments, the following criteria were selected to promote half-maximal binding of mesangial cells: 2.5 μg/ml cIV and a short term assay (less than 30 min). The ability of neutralizing Mabs to inhibit mesangial cell adhesion to cIV was examined in low (5 mM) or high glucose (25 mM) containing media.

To test Mab-mediated adhesion inhibition of mesangial cells grown in 5 mM glucose or 25 mM glucose to collagen IV, $^{35}$S-methionine labeled human mesangial cells were seeded in 48 well plates (100,000 cells/well) coated with 200 μl cIV (2.5 μg/ml, overnight at 29° C.). Mab's anti-α1, SR84, anti-α2, P1H5, anti-β1, P5D2 and SR84 and P1H5 together, were added to the wells before seeding with cells. Adhesion in the presence of W6/32 was used as a control. After 20 minutes non-adherent cells were washed out and adherent cells quantitated. The data was expressed as a percentage of the binding in the presence of W6/32, and the two cell populations were normalized by using the binding in the presence of HLA antibody to represent 100% and the inhibition by other antibodies was calculated as a percentage of binding in the presence of HLA.

The results indicated that the α1β1 integrin receptor had a reduced role (*p<0.001) for cells grown in 5 mM glucose as compared with 25 mM glucose. Of the antibodies examined, only Mabs directed to the α1 (SR84), α2 (P1H5) or β1 (P5D2) integrin subunits inhibited the binding of mesangial cells to cIV. When mesangial cells were grown in either low or high glucose, adhesion to cIV could be almost completely inhibited with Mabs to β1 (P5D2) or a combination of α1 (SR84) and α2 (P1H5).

The relative effects of the neutralizing Mabs directed against the α1 and α2 subunits varied depending on whether mesangial cells were grown in low or high glucose. In 5 mM glucose the Mab to the α1 subunit of integrins resulted in more inhibition (≈50%) than in 25 mM glucose (≈20%) (p<0.001). This is consistent with the presence of significantly more α1 integrin on the surface of cells grown in 5 mM glucose. Alternatively, in 5 mM glucose the Mab to the α2 subunit resulted in less inhibition (≈60%) than in 25 mM glucose (≈75%) (p<0.001). Mab's against the α3, α4, α5 and α6 subunits did not inhibit adhesion (data not shown).

These data demonstrate that under low glucose growth conditions, mesangial cells use α1β1 and α2β1 integrins to bind cIV coated surfaces. However, cells grown in high glucose, appear to rely more on the α2 subunit complexed with β1. The results of these functional studies are consistent with the observed alterations in the integrin cell surface phenotype discussed in Example 1.

EXAMPLE 3

Localization of α1β1 and α2β1 Integrin Receptors

Localization of α1 Integrin in Focal Adhesions

Glass cover slips were coated with 50 μl of cIV at 2.5 μg/ml, overnight at 29° C. The coated areas were "blocked"

for two hours with BSA at 2 mg/n, in PBS. Human mesangial cells were processed as before, seeded on each spot of cIV in 50 µl of binding buffer (2500 cells) and allowed to adhere for 5 hours at 37° C. The unbound cells were washed off with PBS. Adherent cells were fixed with 2% paraformaldehyde in HBSS for 30 minutes followed by permeabilization with 0.5% Triton X-100 for 2 minutes. The cells were blocked again with PBS following which 200 µl of hybridoma culture supernatant containing anti-al antibody (TS1/7) was added to each spot and incubated at room temperature for 1 hour. The coverslips were then thoroughly washed and rhodamine-conjugated goat anti-mouse antibody (1:100) (Boehringer Mannheim, Indianapolis, Ind.) was added for one hour. The coverslips were again washed and incubated with anti-vinculin antibodies (Sigma, St. Louis, Mo.) pre-conjugated (Quicktag, FITC labeling kit, Boehringer Mannheim, Indianapolis, Ind.) to FITC labeled goat anti-mouse antibody for 1 hour at room temperature. The coverslips were finally washed, mounted on glass slides and viewed for focal adhesions by co-localization of vinculin with α1 integrin.

Staining of Normal Human Adult Kidneys for the Presence of α1Integrins

Normal human adult kidney tissue was snap frozen in liquid nitrogen and sections were prepared with a cryostat at 5 µm intervals. The sections were stained using an anti-mouse Vectastain Elite Kit (as described by Wayner et al., 1993) with diamino benzene (DAB) as the chromogen. The following mAbs were used: α1 (TS2/7), α2 (P1H5), α3 (P3D11), α4 (P4G9) and β1 (P5D2). These monoclonal antibodies are available from the following sources and stained the following histological areas as was demonstrated in these studies:

| | |
|---|---|
| α1 (TS2/7) | Martin Hemler, Dana Farber Cancer Center, Boston, MA. Stained mesangium. |
| α2 (P1H5) | E A Wayner, Fred Hutchinson Cancer Center, Seatle, WA Stained mesangium. |
| α3 (P3D11) | E A Wayner, Fred Hutchinson Cancer Center, Seattle, WA Stained the mesangium, endothelium, visceral and Bowman's epithelium and capsule. |
| α4 (P4G9) | E A Wayner, Fred Hutchinson Cancer Center, Seattle, WA Did not stain glomeruli. |
| β1 (P5D2) | E A Wayner, Fred Hutchinson Cancer Center, Seattle, WA Stained mesangium, endothelium, visceral epithelium, Bowman's epithelium and capsule. |

Normal Mouse IgG (all isotypes) was Used as a Negative Control.

These studies demonstrated the presence of α1β1 and α2β1 integrin receptors in focal adhesions. Focal adhesions are observed when cells spread in culture on matrix components such as collagen IV, fibronectin or laminin. Integrins cluster at the site of focal adhesions on the cell surface with intracellular fibers such as vinculin staining at these locations within the cell periphery. (see Hynes, et al. *Cell* 69:11–25, 1992 and Burridge, et al. *Ann Rev. Cell Biol.* 4:487–525, 1988). This supports the hypothesis that mesangial cells use α1β1 and α2β1 integrin receptors to bind to cIV. It has been well established that when a particular integrin receptor is engaged by a specific ligand it can be detected in focal contacts co-localized with certain components of the cytoskeleton such as vinculin. Therefore, we asked whether mesangial cells could localize α1 (or α2 and β1) to focal adhesions when seeded on cIV coated substrates.

α2 or β1 could be detected in focal contacts on cIV regardless of whether mesangial cells were grown in either low or high glucose. Additionally, when mesangial cells were grown in 5 mM glucose and subsequently seeded on cIV coated surfaces, α1 could also be co-localized with vinculin within several focal contacts by dual-label immunofluorescence staining. It is believed that cIV binding in cells maintained in low glucose engages both the α1 and α2 subunits. α1 could be detected in only some of the focal adhesions stained by vinculin. As a control, α1 was not detected in focal contacts when mesangial cells were seeded onto fibronectin coated surfaces regardless of the glucose concentration of the cell culture media.

Immunohistochemical staining of integrin receptor subunits in normal human adult and fetal kidney revealed that both α1 and α2 could be localized within the mesangium. The α1 receptor was diffusely expressed throughout the mesangium whereas the distribution of α2 was more limited and focal. Also consistent with the results we obtained with cultured mesangial cells, β1 and α3 were intensely expressed throughout the mesangium, while α4 could not be detected in either fetal or adult mesangium.

EXAMPLE 4

Alterations in RNA Production in Human Mesangial Cells Cultured in High and Low Glucose Concentrations Our efforts have concentrated on finding a way to predict, at early stages after the onset of diabetes, the subjects who will later develop nephropathy. We focused on a major hallmark of diabetic nephropathy, that of mesangial expansion. We first examined mesangial cells in culture, since these cells secrete their surrounding matrix, which is expanded in diabetes; however, biopsied tissue can be treated in the same manner, as will be understood by those skilled in the art. The matrix consists primarily of collagen IV.

Primary cultures of human mesangial cells undergo several phenotypic changes in response to elevated glucose concentrations and glucose-modified ("glycated") collagen IV. These changes included altered cell interactions with the collagen matrix. In elevated glucose concentrations, the α1 subunit underwent a substantial decrease, concomitant with an increase of the α2 integrin subunit. This change was observed with immunoprecipitation and flow cytometry. Further studies with Northern analysis and in situ hybridization of the cultured mesangial cells confirmed the integrin reversal. In the studies employing Northern analyses, separate samples of total RNA were isolated from the mesangial cells on each culture plate or alternatively from rat kidneys (see Example 5, below) by a single-step method using RNA STAT-60™ isolation reagent (TEL-TEST "B", INC., Friendswood, Tex.) according to the manufacturers directions. Briefly, the cells were lysed with RNA STAT-60™ solution by repetitive pipetting; the tissues were cut into small pieces and homogenized in the RNA STAT-60 solution with a high-speed tissue homogenizer (Polytron CH6005, Luzern, Switzerland). The nucleic acid mixture was extracted with 0.2 ml chloroform per 1 ml of the RNA STAT-60™ solution. Total RNA was precipitated for 10 min at –80° C. in isopropanol, and the pelleted RNA was redissolved in TE buffer. The total RNA was free of DNA and proteins and had a 260/280 wavelength ratio>1.8.

Northern blot analysis-The RNA samples were denatured in formaldehyde gel-running buffer (20 mM MOPS, 8 mM sodium acetate, mM EDTA, at pH 7.0) containing 6% formaldehyde and 50% formamide by heating at 65° C. for 15 min. For each sample 20 mg of RNA was mixed with 6x loading buffer (50% glycerol, 1 mM EDTA, 0.25% bromphenol blue, 0.25% Xylene cyanol FF), loaded on 1% agarose gel submerged in 6% formaldehyde running buffer, and run at 3–5 V/cm for 3–4 hours. RNA was transferred from the agarose gel to a nylon membrane (Boehringer Mannheim, Indianapolis, Ind.) by capillary elution and immobilized by U V cross-linking (Stratalinker U V; Stratagene, La Jolla, Calif.). The membranes were then incubated in prehybridization solution containing 50% formamide, 5xSSC. 0.02% SDS, 0.1% N-lauroylsarcosine, 2% blocking reagent (Boehringer Mannheim), and 20 mM sodium maleate (pH 7.5) for >3 hours at 42° C. Radiolabeled probes (see Example 5) for the integrin subunits or controls were then added to the prehybridization solution and hybridization was performed overnight at 42° C. (for cDNA probe) or 50° C. (for antisense RNA probe). After hybridization, the membranes were initially washed in 2xSSC, 0.05% SDS for 10 minutes at room temperature and then washed for an additional 40 minutes at 42° C. (for cDNA probe) or 60° C. (for antisense RNA probe). Membranes were then exposed to X-ray film (X-Omat RP; Eastman Kodak Co., Rochester, N.Y.) for 1 day at −80° C. After being stripped of previous probes by heating in 0.2xSSC, 0.5% SDS for 10 min at 100° C., the membranes were reprobed as described above. Images of autoradiograms were captured and digitized using a CCD video camera module interfaced with a microcomputer (Macintosh IIcx: Apple Computers Inc., Cupertino, Calif.) and analyzed using image processing software (NIH Image 1.55b77: public domain).

Cells grown in 25 mM glucose expressed lower levels of $\alpha 1$ integrin than seen in an equivalent amount of RNA from cells grown in 5 mM glucose. Densitometric analysis demonstrated an ≈30% decrease upon averaging the values from four samples. Similar analysis demonstrated ≈30% increase in $\alpha 2$ integrin expression in cells grown in 25 mM glucose.

EXAMPLE 5

In Situ Hybridization Detecting Expression of Integrins in Kidney Sections Taken at Various Times After Onset of Diabetes The expression of $\alpha 1$ and $\alpha 2$ integrin receptors was examined in rat kidney sections after the onset of diabetes.

The in situ hybridization approach was used to examine kidney sections of streptozotocin-diabetic rats, 2.5 months after induction of diabetes. At this time interval, glomerular changes were still minimal. The streptozotocin-induced diabetic rat model mimics human changes of mesangial expansion and glomerular basement membrane thickening in late nephropathy and is an art accepted model for diabetes and nephropathy.

Female non-pregnant Sprague-Dawley rats were obtained from Brithwood, Minneapolis, Minn. The animals weighed 190–210 g at the beginning of the experiments and were given a 52 mg/kg intraperitoneal dose of streptozotocin (STZ, Zanazar brand, Upjohn Corp., Kalamazoo, Mich.) in calcium citrate and calcium carbonate Buffer (pH 4.5) to induce diabetes, while the controls were injected with the same amount of Hanks' balanced salt solution (pH 7.2). The animals were fed on standard rat chow (Purina laboratory chow # 5001. RFG PET@Supply Company, Plymouth, Minn.), and tap water ad libitum. Presence of diabetes was confirmed by detection of >400 mg/dl nonfasting plasma glucose levels 10 days post injection by tail vein bleeding using the glucose peroxide method (Beckman glucose analyzer, Beckman Instruments, Inc., Fullerton, Calif.).

Body weight was determined weekly, blood glucose levels were determined at 4 weeks after induction of diabetes, and on the day before the termination of the experiment, which was 2.5 month from induction of diabetes. Urinary albumin excretion (UAE) was determined by radial immunodiffusion Mancini method, using goat IgG fraction against rat albumin (Cappel Cat. No. 55727) and purified rat albumin (Cappel Cat. No. 55952, Cappel Research Products, Durham, N.C.), according to previously published procedures (Mauer et al, *Diabetes* 27:959–64, 1978). Rats were sacrificed at 2.5 months after diabetes induction and kidney tissue was perfusionally fixed by injecting freshly prepared 4% paraformaldehyde through the renal artery. This was followed by overnight fixation in 4% paraformaldehyde after removal from the body. The tissue was sectioned at 5 μm and placed on the silane-coated slides (Digene Diagnostics, Inc., Beltsville, Md.) for in situ hybridization with probes for the $\alpha 1$ and $\alpha 2$ integrin subunits.

2.5 months after injection of STZ, diabetic rats weighted significantly less than controls, whereas their right kidney weight and serum glucose concentration were significantly increased, as compared to the controls (see Table 1). Diabetic and non-diabetic rats demonstrated no significant difference in glomerular size and albumin excretion at 2.5 month after induction of diabetes (Table 1).

TABLE 1

| TISSUE | CONTROL | DIABETIC | S/NS |
|---|---|---|---|
| Body Wt. (g) | 390+/−10 | 200+/−20 | S |
| Right Kidney wt. (g) | 1.35+/−0.1 | 1.8+/−0.1 | S |
| Plasma glucose (mg/dl) | 140+/−25 | 760+/150 | S |
| Glomerular area | 1.42+/−0.5 | 1.45+/−0.6 | NS |

A 5.4 kb human $\alpha 2$ integrin cDNA clone (Takada, et al., 1989, supra) and a rat $\alpha 1$ integrin cDNA clone (Ignatius et al, supra) in bluescript vector (Stratagene, La Jolla, Calif.) were used in these experiments. A 1.79 kb $\alpha 2$ integrin cDNA fragment was restriction digested from the EcoRI site. Similarly, $\alpha 3.98$ kb $\alpha 1$ integrin cDNA fragment was obtained by restriction digestion from the EcoRI site.

cDNA fragments were purified by GENE CLEAN II kit (BIO 101, San Diego, Calif.) and labeled using the random primer labeling kit (Boehringer Mannheim, Indianapolis, Ind.) with $P^{32}$-dCTP (NEN) for Northern blotting and with $S^{35}$-dCTP (NEN) for in situ hybridization. GAPDH and sheep visna virus cDNA (PLV-KS) (Staskus et al, *Virology* 181:228–240, 1991) probes were used as the positive and negative controls respectively. The probes preferably had a specific activity of $2 \times 10^8 - 1 \times 10^9$ dpm/μg.

By Northern blotting, compared to the controls, the diabetic kidneys expressed 113.5% more $\alpha 1$(IV) RNA, 46.5% more $\alpha 3$(IV) RNA, 54.8% less metalloproteinase-2 RNA (MMP-2, an enzyme that cleaves type IV collagen) and 246% more TIMP-1 RNA (a tissue inhibitor of metalloproteinases) with a p<0.01 in all cases as determined by ANOVA.

The expression of $\alpha 1$ and $\alpha 2$ integrin RNA was localized using a modification of a previously described method for in situ hybridization (Staskus et al. supra). 5μm tissue sections on silane-coated slides were fixed in the freshly prepared 4% paraformaldehyde for 10 min. The slides were pretreated with 0.2N HCl for 20 min, 0.15 M Triethanolamine (TEA, Sigma, St. Louis, Mo.) for 15 min, 0.005% digitonin for 5 min, 3 mg/ml proteinase K (Sigma) for 15 min at 37° C., and 0.3% acetic anhydride–0.1M TEA for 10 min. Hybridizations were performed under stringent hybridization conditions. Stringent hybridization conditions are defined in this specification as 50° C. overnight, in 50% formamide, 0.6 M NaCl, 1× Denhardt's solution, 0.17 mg/ml human $COT^{RT}$ DNA (GIBCO/BRL), 1 mg/ml poly A (Boehringer Mannhieim), 10% (w/v) Dextran sulfate (Sigma), 0.1 M dithiothreitol (DTT, Boehringer Mannheim), 1 mM EDTA, 0.1 mM aurinitricarboxylic acid (ATA, Sigma) and $S^{35}$-dCTP labeled cDNA probe. The next day, the slides were washed in 2×SSC-0.05% SDS for 60 min at 55° C. (recipes for SSC and the like can be found in Sambrook, et al., supra); further washed in a high stringency washing buffer containing 50% formamide, 0.6 M NaCl, 1 mM EDTA, 5 mM DTT and 10 mM Hepes for 4 days at room temperature. After a brief rinse in 2×SSC, the slides were dehydrated in graded ethanol with 0.3 M ammonium acetate then dipped in Kodak NTB-2 emulsion and exposed for 5 days at 4° C.

After development the slides were stained with hematoxylin-eosin (Surgipath Canada, Inc., Winnipeg, Canada) and mounted. A ratio of the number of silver grains per cell was used to quantitate the results of in situ hybridization. Twenty glomeruli each were counted from each control and diabetic animal. Each glomerulus was assessed for: 1) glomerular area; 2) glomerular perimeter, 3) grains per glomerulus; and 4) number of cell nuclei per glomerulus.

The results were estimated as grains per cell nucleus and grains per glomerular area, as mean +/– SD of 5 animals (20 glomeruli each). (Haase, A. T., [1990]: *In situ hybridization*, CRC Press, 199–217; Nuovo, G. J., [1992] *PCR in situ hybridization, protocols and applications*, Raven Press). Groups were compared with the 2-tailed student t-test. Differences between groups were considered significant at p<0.05.

The results are illustrated in FIG. 1. Early after induction of experimental diabetes, the expression of the α1 integrin subunit by glomerular cells was decreased compared to the control, whereas the expression of α2 integrin was increased. The average counts, in diabetic glomeruli hybridized with the α1 integrin probe, were significantly lower than control (FIG. 1). Also, the average counts, in diabetic glomeruli hybridized with the α2 integrin probe, were significantly higher than control (FIG. 1).

Control animals at 2.5 month diabetes expressed on an average a significantly higher level of α1 subunit integrin and significantly lower levels of α2 subunit integrin using unbiased methods of selection of areas for study. The entire section was surveyed for RNA grains, the regions of the Bowman's space and the background count were excluded by studying a commensurate area of the negative control stained tissue.

Compared to the control, glomerular cells (GC:endothelial, epithelial and mesangial combine) and/or tubular (proximal and distal epithelial) cells (TC) had 36% (GC) less grains for α1 integrin; 86.4% (GC) more grains for α2 integrin; 82(TC)-167% (GC) more grains for α1(IV); 107 (TC)-137% (GC) more grains for α3(IV); 63.6(GC)-65.3%(TC) less MMP-2.

The results of the present study clearly demonstrate that mesangial cells, when cultured in high glucose (25 mM) instead of normal/low glucose (5 mM) alter their RNA production for the integrin subunits α1 and α2. Thus, this phenomenon is observed both at the level of protein and RNA production.

Furthermore, the results of our in situ hybridization and immunohistochemical staining experiments show that these changes can be detected in the mesangium of diabetic rat kidney and that human α2 integrin subunit probes and rat α1 integrin subunit probes are functional in both rat and human cells. Work by Mendrick and co-workers (*Lab. Invest.* 72(3):367–375, 1995) has shown that in the rat both integrins α1β1 and α2β1 of mesangial cells interact with collagen; as happens in the human mesangial cells. In the present study, the distribution of α1 and α2 integrin receptor subunit RNA was precisely localized by in situ hybridization to the different cell types of the glomerulus and surrounding tubules. Normal rat tissues expressed levels of the α1 subunit and also the α2 subunit RNA, as determined by counting the number ratio of silver grains/cell. However, the streptozotocin-induced diabetic animals had significantly lower levels of RNA for the α1 subunit and significantly higher levels of α2 subunit. A similar distribution of α1 and α2 subunit RNA (silver grains) was seen in the proximal and distal tubular epithelial cells. These data indicate that the distribution of cell surface integrin expression may be regulated by gene expression at the transcriptional level.

In summary, using in situ hybridization, similar results were seen in both mesangial cells in vitro and in glomeruli from tissue sections probed for the α1 and α2 integrin.

Early after induction of streptozotocin-diabetes in rates, substantial matrix-related gene expression changes occurred. For example, α1 and α2 integrin levels changes, components of α1β1 and α2β1 integrin cell receptors for tIV (an important component of the renal extracellular matrix) underwent a reversal in levels with less α1 and more α2 integrin being present in glomeruli from kidneys of diabetic rats, when compared to the control. Expression of tIV was increased whereas the expression of MMP-2 which degrades tIV was substantially decreased. TIMP-1, an inhibitor of MMP-2 was increased. The observed matrix changes indicate an imbalance of tIV synthesis and turnover. This dysmetabolism of tIV, apparent in both the glomerular and tubular areas of the kidney, occurred before significant renal functional changes, or matrix accumulation out of proportion to renal enlargement, could be detectable. These changes could have a regulatory role in significant basement membrane thickening and mesangial expansion of diabetic nephropathy.

Collectively, the obtained data indicate that increased glucose concentration induces quantitative changes in receptor synthesis and cell surface integrin expression of human mesangial cells. In the diabetic, all cell systems are exposed to hyperglycemia and it is know that many cell and organ systems are affected by the disease; therefore, other cell types could similarly be used to assess changes in the levels of α1 and/or α2 integrin subunit expression as a measure of a predisposition to a variety of diabetic-induced pathologies. Kyu-Jin, et al. (supra) have noted alterations in integrin subunit expression in skin fibroblasts of diabetic patients. This information, in conjunction with the data discussed herein, indicates that altered levels of integrin subunit expression can be detected from a variety of integrin-expressing cells in diabetic nephropathy patients.

These results support the in vitro primary human mesangial cell culture data demonstrating that changes in cell surface integrin expression indicate the onset of nephropathic changes.

EXAMPLE 6

Detection of Altered Levels of α1 and α2 Integrin Subunit Expression in Humans Using Blood and Tissue Sample Patients with insulin-dependent diabetes mellitus (IDDM), individuals at risk for developing IDDM, patients with clinical diabetes nephropathy and healthy age matched volunteers are selected for studies to confirm the presence of altered α1 and α2 integrin subunit expression in integrin-producing cells. Clinical diabetic nephropathy is defined by the presence of persistent proteinuria (urinary AER>300 µg/day) in sterile urine of patients with >10 yr duration of disease and concomitant retinopathy and is confirmed by the presence of classic glomerulosclerotic lesions on renal biopsy. Normal, nondiabetic individuals without a family history of hypertension serve as control subjects.

Patients were biopsied as follows: For skin biopsies, a biopsy is taken from the anterior surface of the left forearm by excision under local anaesthetic such as ethyl chloride, see Trevisan, et al. *Diabetes* 41:1239–45, 1992. The biopsy is optionally divided in half. With half of the tissue frozen immediately in liquid nitrogen and the other half placed in Hanks balanced salt solution. The frozen tissue is embedded in paraffin and processed for in situ hybridization as has been described above. A portion of the intact tissue is preferably immediately minced and processed for RNA isolation using techniques described above. Remaining minced tissue is gently digested with trypsin to obtain a cell suspension, washed in media containing serum to remove trypsin and plated onto tissue culture dishes containing 10% FCS supplemented DMEM with antibiotics.

Renal biopsies were obtained as follows. Patients should have normal blood pressures, normal coagulation values and platelet counts. Ultrasound was used to precisely localize the kidney. Ultrasound was also used to determine renal size, structural defects and post-void residual urine. Renal biopsies were performed on sedated patients using the Franklin modified Vim-Silverman or Truecut needles available from surgical supply suppliers. The biopsy specimens were immediately examined under a dissecting microscope to ensure that adequate samples of glomeruli were present for subsequent studies to quantitate integrin levels. Biopsied tissue was sectioned and processed for in situ hybridization as described in Example 5. In one example, renal samples from diabetic patients who did not show signs of microalbuminuria, but who had diabetic siblings with renal nephropathy were processed for in situ hybridization and PCR in situ hybridization. Renal samples from diabetic patients without a family history of nephropathy were also studied by PCR in situ hybridization to detect altered levels of integrin subunit expression.

PCR in situ hybridization is performed as follows. Sections are fixed as described in Example 5 and rinsed in RNase free water. The protocol used is that described by Nuovo, et al. (*Am. J. Surg. Pathol.* 17:683–690, 1993.) Cells are treated with pepsin and DNase as described. cDNA synthesis is initiated by adding 10 µl of a solution containing one or more of the following probes listed in a 5'-3' orientation with their SEQ ID NOS and their nucleic acid location on the respective integrin gene with reverse transcriptase (Perkin-ELmer, Norwalk, Conn.):

| | SEQ ID NO | NA location |
|---|---|---|
| α1 integrin primer | | |
| CCAGAGTCACTCTCACAGAG | 5 | 2729–2748 |
| CACAGCGTACACGTACACC | 6 | 1991–2009 |
| CACTTATAGACATCTCCAG | 7 | 646–664 |

| | SEQ ID NO | NA location |
|---|---|---|
| α2 integrin primer | | |
| CATCCATGTTGATGTCTG | 8 | 1733–1750 |
| CATGTGATTCACCGTCAG | 9 | 894–910 |
| GCATATTGAATTGCTCCGAATGTG | 10 | 801–826 |

The resulting cDNAs are subjected to amplification containing a 1 µM concentration (each) of one or more of the above primers with a paired primer located 5' to the primers provided above. Those skilled in the art will recognize that a variety of other primers could also be used from the α1 and α2 integrin gene sequence to similarly perform PCR in situ hybridization. The preferred primers paired with the above primers are provided below.

| | SEQ ID NO | NA location | SEQ ID Pair |
|---|---|---|---|
| α1 integrin primer | | | |
| GGCGTATGCACAACGCA | 11 | 2261–2277 | 5 |
| GCGACAGCTGACCAGTCAGCA | 12 | 1509–1529 | 6 |
| CACTCCTCCACAGCTCCT | 13 | 251–268 | 7 |
| α2 integrin primer | | | |
| ACATGTACTCACTGG | 14 | 1593–1608 | 8 |
| CTCACATGTGGTCCTCTG | 15 | 433–451 | 9 |
| GTCCTGTTGACCTATCCACTGC | 16 | 296–319 | 10 |

The SEQ ID Pair in the above table refers to the paired primer that provides amplification of the sequence positioned between the primer pairs on the respective integrin gene. The PCR products are detected by using an antidigoxigenin-alkaline phosphatase conjugate and the chromagen nitroblue tetrazolium (NBT)5-bromo-4-chloro-3-indoylphosphate toluidinium (Salt) (BCIP). The counterstain nuclear fast red is used to stain nuclei. Internal probes located within the nucleic acid regions amplified by PCR can also be used to identify the amplified fragments. Thus, based on the pairings provided above, oligonucleotide probes can be selected between regions 267–645, 1530–1990 and between 2278–2728 for the α1 integrin gene and between regions 320–800, 452–893, 1607–1732 for the α2 integrin gene and hybridized and stained following the in situ hybridization methods detailed in Example 5.

A blood sample is also taken from the patient and leukocytes are isolated from blood by centrifugation, followed by hypotonic shock of residual blood cells. The leukocytes are then processed for in situ hybridization as has been discussed in the preceding examples.

Results:

PCR in situ hybridization with renal tissues demonstrated decreased α1 and increased α2 integrin subunits in the patient with diabetic neuropathy as compared with control tissue.

Quantitative analysis of RNA grains per unit area of kidney glomeruli and tubules was performed by counting silver grains under epi-polarized light.

As shown in Table 2, both glomenili and tubules of the diabetic neuropathy patient showed significantly decreased α1 integrin levels as compared to the control, whereas α2 integrin levels were significantly increased as compared with control levels.

TABLE 2

| Sample | Glomeruli[a] | | Tubules[a] | |
| --- | --- | --- | --- | --- |
| | α1 | α2 | α1 | α2 |
| Control | 156 | 83 | 136 | 101 |
| Diabetic Neuropathy | 121[b] | 95[c] | 89[c] | 124[b] |

[a] = grains per unit area
[b] = $p < 0.05$
[c] = $p < 0.01$

These results confirm the in vitro observations in mesangial cells that there is a decrease of the α1 integrin subunit and a concomitant increase of α2 integrin expression in a diabetic nephropathy. This represents a reversal of mesangial integrins which mediate binding of mesangial cells to collagen IV.

EXAMPLE 7

Increased Integrin Subunit Expression in Skin Fibroblasts from Diabetic Patients with Nephropathy as Compared with Control Diabetic Patients Fibroblasts were obtained from skin biopsies from diabetic patients with or without diabetic nephropathy and cultured as described for Example 6. Expression of α3, α5, and beta-1 integrin subunits in the cultured cells was analyzed by Northern blotting and subsequent densitometry, as described above, and using published probes.

For the α3 integrin subunit, the 1.9 SalI fragment described in Takada Y., et al., *J. Cell Biol.* 115:257–266 was used. For the β1 subunit, the 3.6 kb insert of the β1 subunit (the whole cDNA), described in Giancotti and Ruoslahti, *Cell* 60:849–850 (1990) was used. For the α5 subunit, the 3.7 kb SalI-Xba insert of the α5 subunit (the whole cDNA) described in Giancotti and Ruoslahti, Supra as used. These probes were radiolabeled and used under the same conditions as those described for Example 6.

The study included five patients per group, five each from the normal, diabetic "slow track" and from the Diabetic "fast track". Both groups of diabetic human subjects had renal function studies and kidney biopsies performed as part of their evaluation as possible candidates for pancreas transplantation. All procedures were approved by the Committee on Human Subjects at the University of Minnesota, and all patients gave written consent. All patients spent one week at the Clinical Research Center (CRC) at the University of Minnesota for pre-pancreas transplant evaluation, during which time they underwent multiple 24-hour urine collections (at least three) for measurements of creatinine clearance and urinary albumin excretion. Blood pressure was measured repeatedly by the CRC nursing staff. HbA1 was used to assess glycemic control. All patients underwent percutaneous kidney biopsy and skin biopsy. Patients were divided into two groups based on criteria of severity of renal lesions determined by morphometric analysis of mesangial functional volume and IDDM duration.

"Normal" samples were kidney biopsies from non-diabetic human subjects, taken to examine for the presence of neoplastic tissue, etc., on which a similar analysis to that performed for the diabetic tissues was done. These subjects underwent similar renal functional studies to make certain that albuminuria, increased creatinine clearance, or hypertension were not present.

The data, shown below in Table 3, demonstrate a significant increase in α3 and beta-1 subunit expression in the skin fibroblasts of diabetic nephropathy patients as compared with the control diabetic patients.

TABLE 3

| Integrin Subunit | Normal Values | Control Diabetic | Nephropathy Diabetics | p |
| --- | --- | --- | --- | --- |
| α3 | 11.5 | 10.1 | 17.1 | <0.5 |
| | (9.1–13.3) | (8.6–12.8) | (16.1–35.6) | |
| α5 | 36.2 | 38.7 | 30.3 | |
| | (18.3–46.6) | (31.6–57.2) | (13.2–48.4) | |
| β1 | 29.9 | 24.9 | 37.1 | <0.5 |
| | (24.0–33.4) | (17.4–30.9) | (24.2–74.6) | |

While particular embodiments of the invention have been described in detail, it will be apparent to those skilled in the art, that these embodiments are exemplary rather than limiting, and the true scope of the invention is that defined in the following claims.

We claim:

1. A method for identifying a mammal having or at risk for developing glomerulonephropathy comprising the steps of:
analyzing integrin subunit expression in a mammalian tissue sample known to contain cells expressing α1 and α2 integrin subunits and in a control tissue sample, wherein said analyzing comprises incubating the sample with an anti-integrin subunit antibody, and
correlating a decreased level of α1 integrin subunit expression or an increased level of α2 integrin subunit expression in the sample tissue as compared with the control tissue with the presence of or risk of developing nephropathy.

2. A method for identifying a mammal having or at risk for developing glomerulonephropathy comprising the steps of:
analyzing integrin subunit expression in a mammalian tissue sample known to contain cells expressing α1 and α2 integrin subunits and in a control tissue sample, wherein said analyzing comprises incubating the sample with an anti-integrin subunit antibody; and
correlating a decreased level of α1 integrin subunit expression and an increased level of α2 integrin subunit expression in the sample tissue as compared with the control tissue with the presence of or risk of developing nephropathy.

3. The method of claim 1, wherein the mammal is a human.

4. The method of claim 1, wherein the tissue sample is a kidney biopsy, a skin biopsy, or blood.

5. The method of claim 1, wherein the control sample is from a mammal having no history of hypertension.

6. The method of claim 1, wherein an increase of about 25%–100% in the level of α2 integrin subunit expression in the sample tissue as compared with the control is correlated with nephropathy.

7. The method of claim 1, wherein a decrease of about 25%–100% in the level of α1 integrin subunit expression in the sample tissue as compared with the control is correlated with nephropathy.

8. A method for identifying a mammal having diabetes who has or is at risk for developing secondary pathological changes associated with diabetes comprising the steps of:
analyzing integrin subunit expression in a mammalian tissue sample known to contain cells expressing α1 and α2 integrin subunits and in a control tissue sample, wherein said analyzing comprises incubating the sample with an anti-integrin subunit antibody; and
correlating a decreased level of α1 integrin subunit expression and/or an increased level of α2 integrin subunit expression in the sample tissue as compared with the control tissue with the presence of or risk of developing secondary pathological changes associated with diabetes.

* * * * *